United States Patent
Salerno et al.

(10) Patent No.: US 10,753,994 B2
(45) Date of Patent: Aug. 25, 2020

(54) SYSTEMS AND METHODS FOR SIMULTANEOUS MULTI-SLICE IMAGING

(71) Applicant: University of Virginia Patent Foundation, Charlottesville, VA (US)

(72) Inventors: Michael Salerno, Charlottesville, VA (US); Yang Yang, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 275 days.

(21) Appl. No.: 15/959,913

(22) Filed: Apr. 23, 2018

(65) Prior Publication Data

US 2018/0306880 A1    Oct. 25, 2018

Related U.S. Application Data

(60) Provisional application No. 62/488,103, filed on Apr. 21, 2017.

(51) Int. Cl.
*G01R 33/483* (2006.01)
*A61B 5/055* (2006.01)
(Continued)

(52) U.S. Cl.
CPC .......... *G01R 33/4835* (2013.01); *A61B 5/055* (2013.01); *G01R 33/583* (2013.01);
(Continued)

(58) Field of Classification Search
None
See application file for complete search history.

(56) References Cited

U.S. PATENT DOCUMENTS

| 7,174,200 B2 | 2/2007 | Salerno et al. |
| 8,700,127 B2 | 4/2014 | Salerno et al. |

(Continued)

OTHER PUBLICATIONS

Adluru G, McGann C, Speier P, Kholmovski EG, Shaaban A, Dibella EV. 2009. Acquisition and reconstruction of undersampled radial data for myocardial perfusion magnetic resonance imaging. J Magn Reson Imaging. 29(2):466-473.

(Continued)

*Primary Examiner* — Paresh Patel
(74) *Attorney, Agent, or Firm* — Meunier Carlin & Curfman LLC

(57) ABSTRACT

Systems and methods for simultaneous multi-slice imaging. In one embodiment, a method for magnetic resonance imaging of a region of interest of a subject includes simultaneously exciting multiple, different slice locations corresponding to a region of interest of a subject using a radiofrequency (rf) pulse, for obtaining multiple slices. The excitation phase is modulated between acquisitions using a phase cycling scheme configured to create signal cancellation of all but one slice of the multiple excited slices from the different slice locations. The method also includes applying an imaging pulse sequence using a spiral k-space trajectory to acquire image data from the multiple slices, for an image or series of images of the region of interest; and reconstructing, from the multiple slices, images of the region of interest, wherein the reconstructing recovers unaliased images from the different slice locations.

35 Claims, 22 Drawing Sheets
(10 of 22 Drawing Sheet(s) Filed in Color)

(51) Int. Cl.
G01R 33/58 (2006.01)
G01R 33/48 (2006.01)
G01R 33/561 (2006.01)
A61B 5/00 (2006.01)
G01R 33/56 (2006.01)
G01R 33/563 (2006.01)

(52) U.S. Cl.
CPC ............ *A61B 5/7257* (2013.01); *A61B 5/7285* (2013.01); *G01R 33/4824* (2013.01); *G01R 33/5601* (2013.01); *G01R 33/5605* (2013.01); *G01R 33/5611* (2013.01); *G01R 33/56341* (2013.01)

(56) References Cited

U.S. PATENT DOCUMENTS

| | | | |
|---|---|---|---|
| 9,224,210 | B2 | 12/2015 | Epstein et al. |
| 2003/0199750 | A1* | 10/2003 | Park ..................... A61B 5/0263 600/410 |
| 2005/0248342 | A1* | 11/2005 | Rottengatter ............ G01V 3/32 324/303 |
| 2008/0284439 | A1* | 11/2008 | Xu ......................... A61B 5/055 324/322 |
| 2009/0082656 | A1* | 3/2009 | Bayram .............. G01R 33/4818 600/410 |
| 2009/0196478 | A1* | 8/2009 | Lustig ................ G01R 33/5611 382/131 |
| 2013/0307536 | A1 | 11/2013 | Feng et al. |
| 2013/0342206 | A1* | 12/2013 | Ugurbil .............. G01R 33/4835 324/309 |
| 2015/0285889 | A1* | 10/2015 | Chen ...................... A61B 5/055 324/309 |
| 2016/0148378 | A1 | 5/2016 | Salerno et al. |
| 2017/0076449 | A1 | 3/2017 | Chow et al. |
| 2017/0112449 | A1 | 4/2017 | Huang et al. |
| 2017/0303312 | A1* | 10/2017 | Agiwal ............. H04W 74/0816 |

OTHER PUBLICATIONS

Barth M, Breuer F, Koopmans PJ, Norris DG, Poser BA. 2016. Simultaneous multislice (SMS) imaging techniques. Magn Reson Med. 75(1):63-81.

Breuer FA, Blaimer M, Heidemann RM, Mueller MF, Griswold MA, Jakob PM. 2005. Controlled aliasing in parallel imaging results in higher acceleration (CAIPIRINHA) for multi-slice imaging. Magn Reson Med. 53(3):684-691.

Chow K, Kellman P, Spottiswoode BS, Nielles-Vallespin S, Arai AE, Salerno M, Thompson RB. 2015. Saturation pulse design for quantitative myocardial t1 mapping. Journal of cardiovascular magnetic resonance: official journal of the Society for Cardiovascular Magnetic Resonance. 17:84.

Donoho DL. 2006. Compressed sensing. Ieee T Inform Theory. 52(4):1289-1306.

Fair MJ, Gatehouse PD, DiBella EV, Firmin DN. 2015. A review of 3d first-pass, whole-heart, myocardial perfusion cardiovascular magnetic resonance. J Cardiovasc Magn Reson. 17:68.

Greenwood JP, Maredia N, Younger JF, Brown JM, Nixon J, Everett CC, Bijsterveld P, Ridgway JP, Radjenovic A, Dickinson CJ et al. 2012. Cardiovascular magnetic resonance and single-photon emission computed tomography for diagnosis of coronary heart disease (CE-MARC): A prospective trial. Lancet. 379(9814):453-460.

Griswold MA, Jakob PM, Heidemann RM, Nittka M, Jellus V, Wang J, Kiefer B, Haase A. 2002. Generalized autocalibrating partially parallel acquisitions (GRAPPA). Magn Reson Med. 47(6):1202-1210.

Jaarsma C, Leiner T, Bekkers SC, Crijns HJ, Wildberger JE, Nagel E, Nelemans PJ, Schalla S. 2012. Diagnostic performance of noninvasive myocardial perfusion imaging using single-photon emission computed tomography, cardiac magnetic resonance, and positron emission tomography imaging for the detection of obstructive coronary artery disease: A meta-analysis. Journal of the American College of Cardiology. 59(19) 1719-1728.

Lipinski MJ, McVey CM, Berger JS, Kramer CM, Salerno M. 2013. Prognostic value of stress cardiac magnetic resonance imaging in patients with known or suspected coronary artery disease: A systematic review and meta-analysis. J Am Coll Cardiol. 62(9):826-838.

Lustig M, Donoho D, Pauly JM. 2007. Sparse MRI: The application of compressed sensing for rapid mr imaging. Magn Reson Med. 58(6):1182-1195.

Lustig M, Pauly JM. 2010. Spirit: Iterative self-consistent parallel imaging reconstruction from arbitrary k-space. Magn Reson Med. 64(2):457-471.

Manka R, Wissmann L, Gebker R, Jogiya R, Motwani M, Frick M, Reinartz S, Schnackenburg B, Niemann M, Gotschy A et al. 2015. Multicenter evaluation of dynamic three-dimensional magnetic resonance myocardial perfusion imaging for the detection of coronary artery disease defined by fractional flow reserve. Circ-Cardiovasc Imag. 8(5).

Meyer CH, Pauly JM, Macovski A, Nishimura DG. 1990. Simultaneous spatial and spectral selective excitation. Magnet Reson Med. 15(2):287-304.

Nagel E, Klein C, Paetsch I, Hettwer S, Schnackenburg B, Wegscheider K, Fleck E. 2003. Magnetic resonance perfusion measurements for the noninvasive detection of coronary artery disease. Circulation. 108(4):432-437.

Otazo R, Kim D, Axel L, Sodickson DK. 2010. Combination of compressed sensing and parallel imaging for highly accelerated first-pass cardiac perfusion MRI. Magn Reson Med. 64(3):767-776.

Pedersen H, Kozerke S, Ringgaard S, Nehrke K, Kim WY. 2009. K-t pca: Temporally constrained k-t blast reconstruction using principal component analysis. Magnet Reson Med. 62(3):706-716.

Pruessmann KP, Weiger M, Scheidegger MB, Boesiger P. 1999. Sense: Sensitivity encoding for fast MRI. Magn Reson Med. 42(5):952-962.

Salerno M, Beller GA. 2009. Noninvasive assessment of myocardial perfusion. Circ-Cardiovasc Imag. 2(5):412-424.

Salerno M, Sica C, Kramer CM, Meyer CH. 2013. Improved first-pass spiral myocardial perfusion imaging with variable density trajectories. Magn Reson Med. 70(5):1369-1379.

Salerno M, Sica CT, Kramer CM, Meyer CH. 2011. Optimization of spiral-based pulse sequences for first-pass myocardial perfusion imaging. Magn Reson Med. 65(6):1602-1610.

Salerno M, Taylor A, Yang Y, Kuruvilla S, Ragosta M, Meyer CH, Kramer CM. 2014. Adenosine stress cardiovascular magnetic resonance with variable-density spiral pulse sequences accurately detects coronary artery disease: Initial clinical evaluation. Circ Cardiovasc Imaging. 7(4):639-646.

Salerno M, Taylor AM, Yang Y, Kuruvilla S, Meyer CH, Kramer CM. 2014. Adenosine stress CMR with variable density spiral pulse sequences accurately detects cad with minimal dark-rim artifacts. J Cardiovasc Magn R. 16(Suppl 1):O58.

Salerno M, Yang Y, McHugh S, Holland E, Pan J, Meyer C, Taylor A, Kramer C. 2017. Clinical evaluation of whole-heart quantitative adenosine stress CMR with motion-compensated 11-spirit. Proc Intl Soc Mag Reson Med. 25:528.

Shin T, Nayak KS, Santos JM, Nishimura DG, Hu BS, McConnell MV. 2012. Three-dimensional first-pass myocardial perfusion MRI using a stack-of-spirals acquisition. Magn Reson Med.69:839-844.

Souza SP, Szumowski J, Dumoulin CL, Plewes DP, Glover G. 1988. Sima: Simultaneous multislice acquisition of mr images by hadamard-encoded excitation. J Comput Assist Tomogr. 12(6):1026-1030.

Stab D, Wech T, Breuer FA, Weng AM, Ritter CO, Hahn D, Kostler H. 2014. High resolution myocardial first-pass perfusion imaging with extended anatomic coverage. Journal of magnetic resonance imaging: JMRI. 39(6):1575-1587.

Wang H, Adluru G, Chen L, Kholmovski EG, Bangerter NK, DiBella EV. 2016. Radial simultaneous multi-slice caipi for ungated myocardial perfusion. Magnetic resonance imaging. 34(9):1329-1336.

Wang Z, Bovik AC, Sheikh HR, Simoncelli EP. 2004. Image quality assessment: From error visibility to structural similarity. IEEE Trans Image Process. 13(4):600-612.

(56) References Cited

OTHER PUBLICATIONS

Weingartner S, Moeller S, Schmitter S, Auerbach E, Kellman P, Shenoy C, Akcakaya M. 2017. Simultaneous multislice imaging for native myocardial t1 mapping: Improved spatial coverage in a single breath-hold. Magnet Reson Med. 78(2):462-471.

Yang Y, Chen X, Epstein FH, Meyer CH, Kuruvilla S, Kramer CM, Salerno M. 2014. Motion-corrected compressed-sensing enables robust spiral first-pass perfusion imaging with whole heart coverage. J Cardiovasc Magn R. 16(Suppl 1):O81.

Yang Y, Kramer CM, Shaw PW, Meyer CH, Salerno M. First-pass myocardial perfusion imaging with whole-heart coverage using L1-spirit accelerated variable density spiral trajectories. Magn Reson Med. 2016, 1375-87.

Yang Y, Zhao L, Chen X, Shaw PW, Gonzalez JA, Epstein FH, Meyer CH, Kramer CM, Salerno M. 2017. Reduced field of view single-shot spiral perfusion imaging. Magnet Reson Med. 79(1): 208-216.

Ye H, Cauley SF, Gagoski B, Bilgic B, Ma D, Jiang Y, Du YP, Griswold MA, Wald LL, Setsompop K. 2017. Simultaneous multislice magnetic resonance fingerprinting (SMS-MRF) with direct-spiral slice-grappa (ds-sg) reconstruction. Magnet Reson Med. 77(5):1966-1974.

Yutzy SR, Seiberlich N, Duerk JL, Griswold MA. 2011. Improvements in multislice parallel imaging using radial CAIPIRINHA. Magn Reson Med. 65(6):1630-1637.

Zhou R, Huang W, Yang Y, Chen X, Weller DS, Kramer CM, Kozerke S, Salerno M. 2018. Simple motion correction strategy reduces respiratory-induced motion artifacts for k-t accelerated and compressed-sensing cardiovascular magnetic resonance perfusion imaging. Journal of cardiovascular magnetic resonance: official journal of the Society for Cardiovascular Magnetic Resonance. 20(1):6.

\* cited by examiner

SYSTEMS AND METHODS FOR SIMULTANEOUS MULTI-SLICE IMAGING

CROSS-REFERENCE TO RELATED APPLICATION

This application claims priority to and the benefit of U.S. Provisional Patent Application 62/488,103 filed Apr. 21, 2017, which is hereby incorporated by reference herein in its entirety as if fully set forth below.

STATEMENT OF RIGHTS UNDER FEDERALLY-SPONSORED RESEARCH

This invention was made with government support under Grant Nos. HL112910 and HL131919, awarded by the National Institutes of Health. The government has certain rights in the invention.

BACKGROUND

First-pass contrast-enhanced myocardial perfusion using cardiac magnetic resonance imaging (CMR) is a valuable method to access patients with suspected coronary artery disease (CAD) providing important diagnostic and prognostic information. However, many clinically available techniques have limited spatial-temporal resolution and ventricular coverage. Recent advances in parallel imaging and compressed sensing have improved the spatial coverage while maintaining spatial-temporal resolution. Some non-Cartesian techniques using radial or spiral techniques have demonstrated good image quality with minimal dark rim artifacts, and have demonstrated accurate detection of CAD in preliminary studies. Over the last few years, there has been increased interest in obtaining full heart coverage using 3D imaging techniques, and multi-center trials have demonstrated diagnostic utility. However, 3D perfusion techniques have limited temporal and spatial resolution. A way to achieve whole-heart coverage is to obtain multiple slices at the same time using simultaneous multi-slice imaging techniques (SMS). SMS has found significant applications in neurological MRI, and has recently been used for cardiac applications. To date, there has been limited application of SMS for spiral trajectories.

It is with respect to these and other considerations that the various aspects of the present disclosure as described below are presented.

SUMMARY

In some aspects, the present disclosure relates to systems and methods for simultaneous, multi-slice imaging. In one aspect, the present disclosure relates to a method for magnetic resonance imaging of a region of interest of a subject. In one embodiment, the method includes simultaneously exciting multiple, different slice locations corresponding to a region of interest of a subject using a radio-frequency (rf) pulse, for obtaining multiple slices. The excitation phase is modulated between acquisitions using a phase cycling scheme configured to create signal cancellation of all but one slice of the multiple excited slices from the different slice locations. The method also includes applying an imaging pulse sequence using a spiral k-space trajectory to acquire image data from the multiple slices, for an image or series of images of the region of interest; and reconstructing, from the multiple slices, images of the region of interest, wherein the reconstructing recovers unaliased images from the different slice locations.

In another aspect, the present disclosure relates to a method for perfusion magnetic resonance imaging of a subject. In one embodiment, the method includes simultaneously exciting multiple, different slice locations corresponding to a region of interest of a subject using a radio-frequency (if) pulse, for obtaining multiple slices. The excitation phase is modulated between acquisitions using a phase cycling scheme configured to create signal cancellation of all but one slice of the multiple excited slices from the different slice locations. The method also includes applying an imaging pulse sequence using a spiral k-space trajectory to acquire imaging data from the multiple slices, for an image or series of images of the region of interest; and rotating the phase of the excitation between heartbeats of the subject to create temporal incoherence of a residual aliasing pattern of aliasing. The method also includes reconstructing, from the multiple slices, images of the region of interest.

In another aspect, the present disclosure relates to a method for magnetic resonance imaging of a region of interest of a subject. In one embodiment, the method includes simultaneously exciting multiple, different slice locations corresponding to a region of interest of a subject using a radio-frequency (rf) pulse, for obtaining multiple slices. The excitation phase is modulated between acquisitions using a phase cycling scheme configured to create signal cancellation of all but one slice of the multiple excited slices from the different slice locations. The method also includes applying an imaging pulse sequence using a non-Cartesian trajectory to acquire imaging data from the multiple slices, for an image or series of images of the region of interest. The method also includes reconstructing, from the multiple slices, images of the region of interest. The reconstructing recovers unaliased images from the different slice locations. The phase of the excitation is rotated between excitations by the golden angle or a temporally uncorrelated matrix to create temporal incoherence of the residual aliasing pattern of the other slices to facilitate compressed sensing reconstruction.

In another aspect, the present disclosure relates to a method for magnetic resonance imaging of a region of interest of a subject. In one embodiment, the method includes simultaneously exciting multiple, different slice locations corresponding to a region of interest of a subject using a radio-frequency (rf) pulse, for obtaining multiple slices. The excitation phase is modulated between acquisitions using a phase cycling scheme configured to create signal cancellation of all but one slice of the multiple excited slices from the different slice locations. The method also includes applying a variable density Cartesian pulse sequence to acquire image data from the multiple slices, for an image or series of images of the region of interest; and reconstructing, from the multiple slices, images of the region of interest, wherein the reconstructing recovers unaliased images from the different slice locations.

In another aspect, the present disclosure relates to a system for magnetic resonance imaging of a region of interest of a subject. In one embodiment, the system includes an excitation pulse generator configured to generate a radio-frequency (rf) pulse to simultaneously excite multiple, different slice locations corresponding to a region of interest of a subject, for obtaining multiple slices. The excitation phase is modulated between acquisitions using a phase cycling scheme configured to create signal cancellation of all but one slice of the multiple excited slices from the different slice locations. The system also includes an imaging data acquisition system configured to acquire image data from the multiple slices, for an image or series of images of the region of interest by applying an imaging pulse sequence using a spiral k-space trajectory or a variable density Cartesian pulse sequence. The system also includes a processor coupled to the excitation pulse generator and imaging data acquisition system and configured to cause the system to perform functions to reconstruct, from the multiple slices, images of the region of interest, wherein the reconstructing recovers unaliased images from the different slice locations.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale. The patent or application file contains at least one drawing executed in color. Copies of this patent or patent application publication with the color drawing(s) will be provided by the Office upon request and payment of the necessary fee.

FIG. 1 at (a) shows spiral perfusion images acquired separately from 4 slice positions. FIG. 1 at (b) shows a Hadamard excitation RF phase modulation pattern as applied to each slice position for MB factors of 1-4. FIG. 1 at (c) shows that, for slices 2-4 there is nearly complete suppression of image with an incoherent residual aliasing artifact that varies by slice position. FIG. 1 at (d) shows combined SMS images for MB factors 1-4, showing the image at slice position 1 with superposition of the aliasing patterns from the other slices as shown in FIG. 1 at (c). By applying phase demodulation, the images from the other slice locations can be generated through phase demodulation (as shown in e, f and g). Images at each slice location have a different aliasing pattern in time due to golden angle rotation of the trajectory, and the residual aliasing can be removed using an SMS-L1-SPIRiT (iterative self-consistent parallel imaging reconstruction) reconstruction in accordance with certain embodiments of the present disclosure.

FIG. 2 at (a) shows a non-selective saturation with an adiabatic BIR-4 pulse used for T1-weighted preparation. Before data acquisition, a spectrally selective adiabatic fat-inversion pulse (SPAIR) is applied for fat saturation. An 8 interleaved spiral trajectory is used with the following design parameters: 6 ms readout per spiral interleave with linear variable density starting density of 1.2× Nyquist to ending density of 0.4× Nyquist. The excitation phase of each slice in the SMS acquisition is modulated using a Hadamard phase cycling scheme to achieve MB factors of 1-4. Full heart coverage may be achieved with MB factor 2, 3, and 4 with 4, 3, or 2 saturation blocks respectively. FIG. 2 at (b) shows the excitation phase modulation angle rotated by the golden-angle between heartbeats using MB factor of 2 as an example.

FIG. 20 shows the raw images for each slice location after binning and demodulation. The last column shows cine frames at multiple phases throughout the cardiac cycle for the two slice positions.

DETAILED DESCRIPTION

Figure 1:
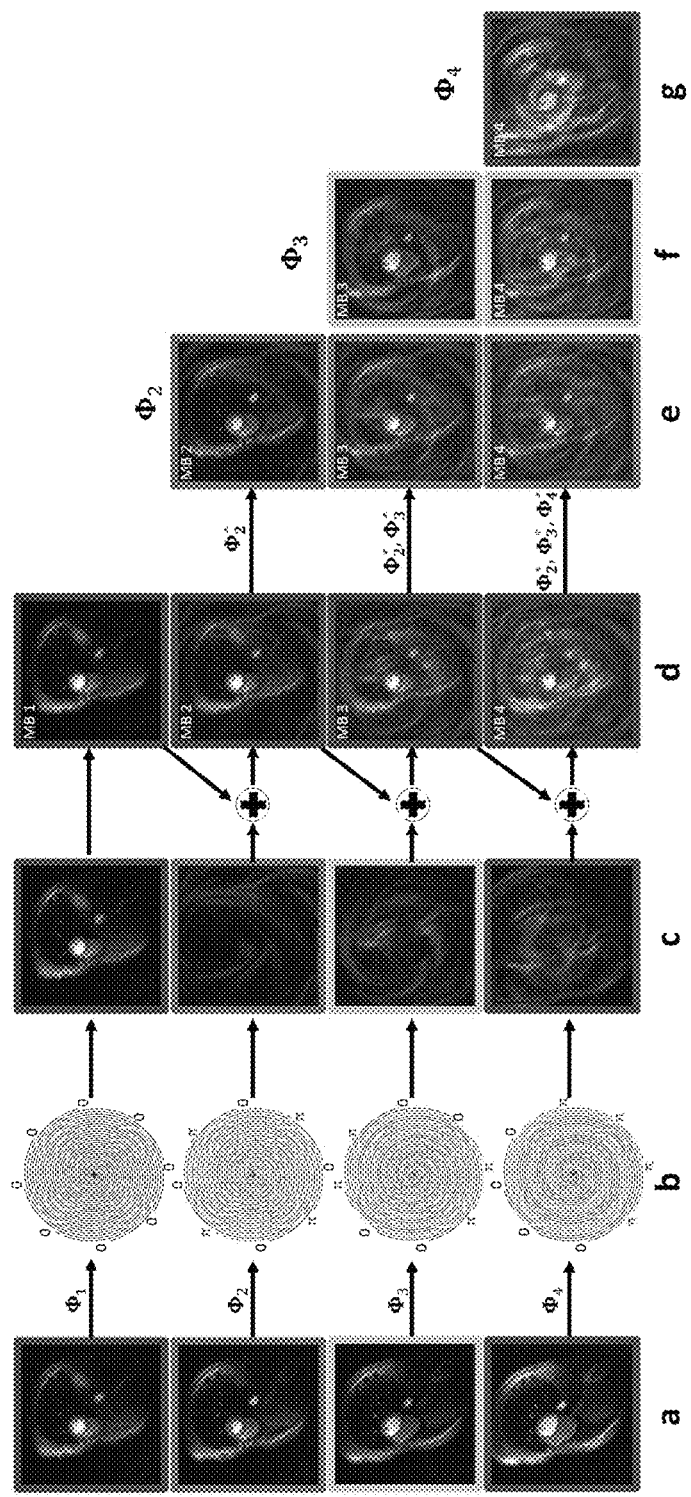
FIG. 1 shows a phase modulation strategy for 8 spiral interleaves at MB=1, 2, 3 and 4, in accordance with one embodiment of the present disclosure.

In some aspects, the disclosed technology relates to systems and methods for simultaneous multi-slice (SMS) imaging. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the $n^{th}$ reference in the list. For example, [3] refers to the $3^{rd}$ reference in the list, namely Lustig M, Pauly J M. 2010. SPIRiT: Iterative self-consistent parallel imaging reconstruction from arbitrary k-space. Magn Reson Med. 64(2):457-471. All references cited and discussed in this specification are incorporated herein by reference in their entireties and to the same extent as if each reference was individually incorporated by reference.

A detailed description of aspects of the present disclosure, in accordance with various example embodiments, will now be provided with reference to the accompanying drawings. The drawings form a part hereof and show, by way of illustration, specific embodiments and examples. In referring to the drawings, like numerals represent like elements throughout the several figures.

Figure 21:
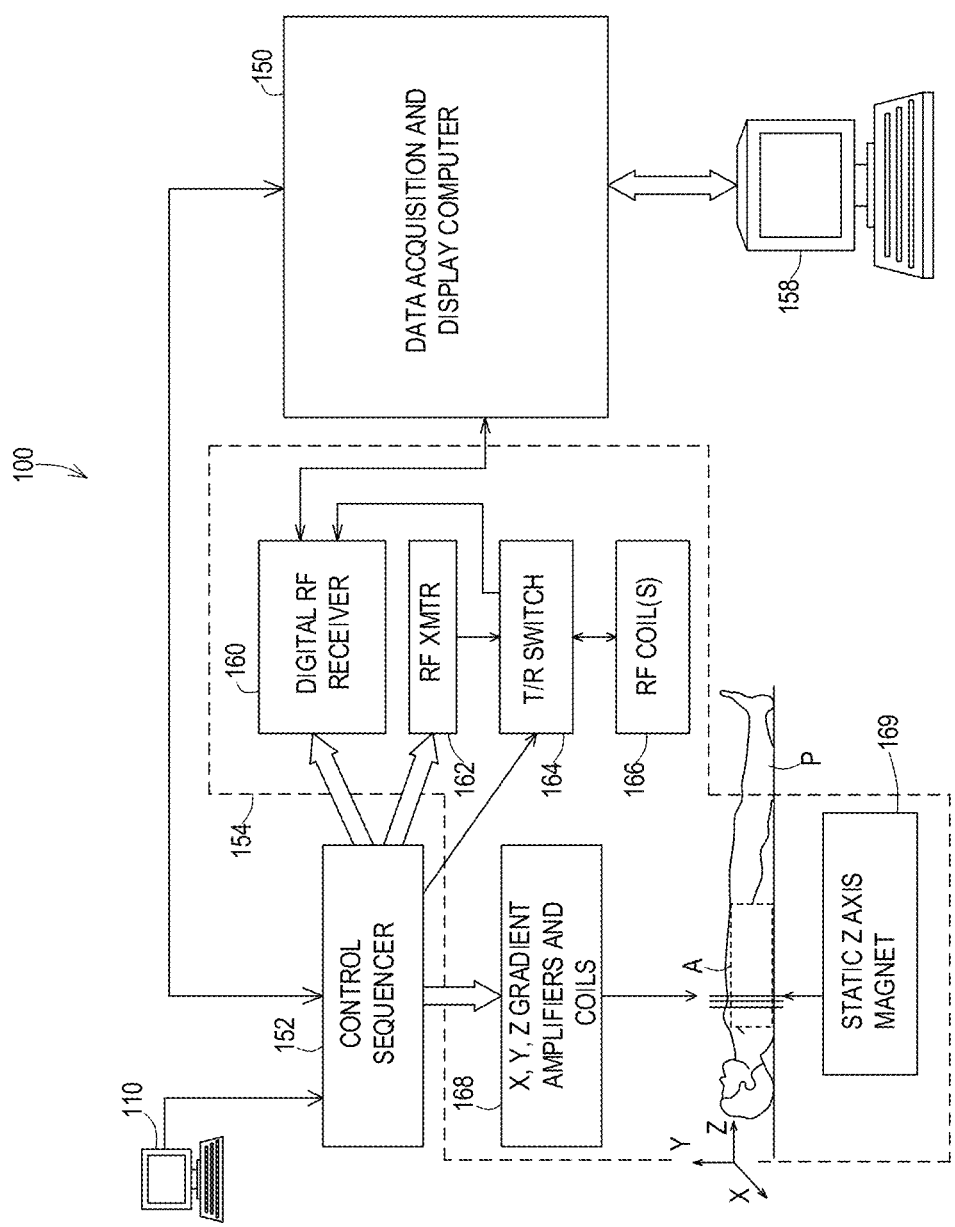
FIG. 21 is a system diagram illustrating a magnetic resonance imaging (MRI) system capable of implementing certain aspects of the present disclosure.

FIG. 21 is a system diagram illustrating a magnetic resonance imaging (Mill) system capable of implementing certain aspects of the present disclosure in accordance with one or more embodiments described herein. The Mill system 100 includes a data acquisition and display computer 150 coupled to an operator console 110, an MM real-time control sequencer 152, and an Mill subsystem 154. The Mill subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MM subsystem 154 may be controlled in real time by control sequencer 152 to generate magnetic and radio frequency fields that stimulate magnetic resonance phenomena in a subject (patient) P to be imaged, for example, to implement magnetic resonance imaging sequences in accordance with various example embodiments of the disclosed technology described herein. An image of an area of interest A of the subject P (which may also be referred to herein as a "region of interest") may be shown on display 158. The display 158 may be implemented through a variety of output interfaces, including a monitor, printer, or data storage.

The area of interest A corresponds to a region associated with one or more physiological activities in subject P. The area of interest shown in FIG. 21 corresponds to a chest region of subject P, but it should be appreciated that the area of interest for purposes of implementing various aspects of the disclosure presented herein is not limited to the chest area. It should be recognized and appreciated that the area of interest in various embodiments may encompass various areas of subject P associated with various physiological characteristics, such as, but not limited to the cardiac functions.

It should be appreciated that any number and type of computer-based medical imaging systems or components, including various types of commercially available medical imaging systems and components, may be used to practice certain aspects of the disclosed technology. Systems as described herein with respect to example embodiments are not intended to be specifically limited to magnetic resonance imaging (Mill) implementations or the particular system shown in FIG. 21.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the disclosed technology may include any device configured to acquire, collect, or otherwise obtain data, or to receive data from a data acquisition device within the system, an independent data acquisition device located on-site or off-site, or another data collection, storage, or processing device.

Figure 22:
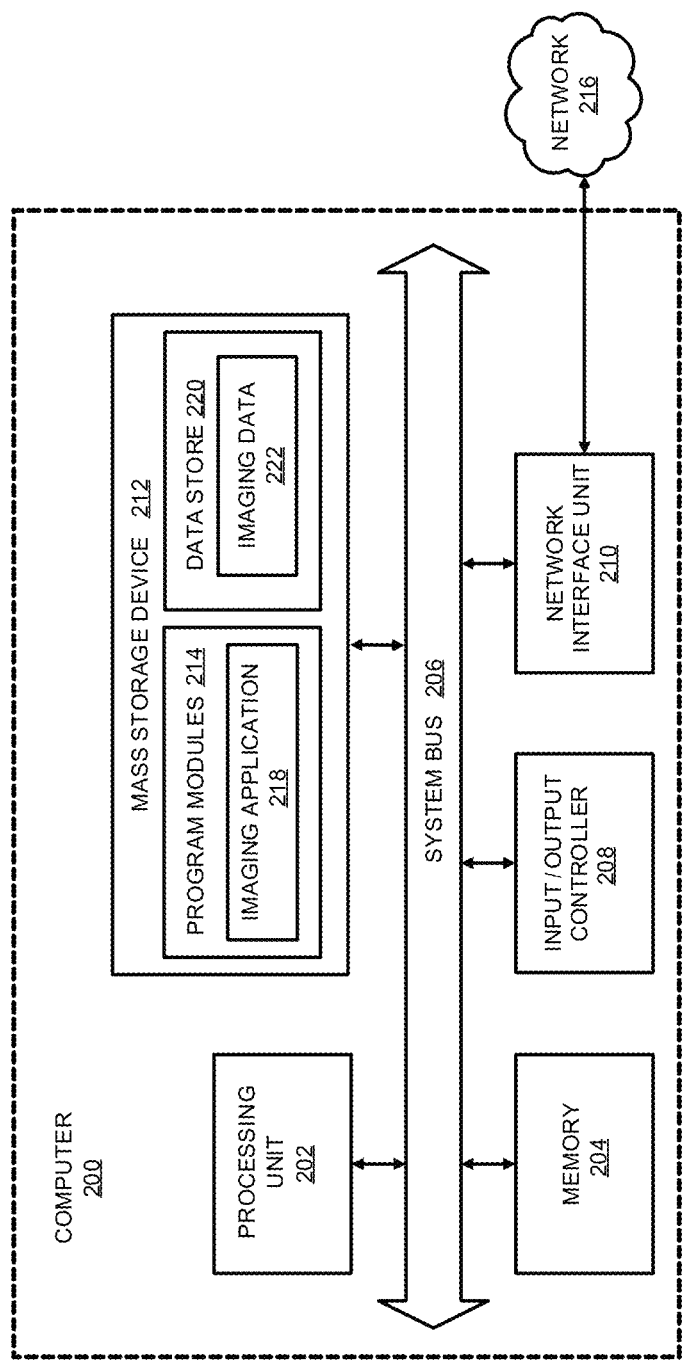
FIG. 22 is a computer architecture diagram showing a computing system capable of implementing certain aspects of the present disclosure.

FIG. 22 is a computer architecture diagram showing a computing system capable of implementing certain aspects of the disclosed technology in accordance with one or more embodiments described herein. A computer 200 may be configured to perform one or more functions associated with embodiments described herein. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 21 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with one or more embodiments discussed above. The program modules 214 may include an imaging application 218 for performing data acquisition and/or processing functions as described herein, for example to acquire and/or process image data corresponding to magnetic resonance imaging of an area of interest. The imaging application 218 may be executed to perform some or all of the functions for simultaneous multi-slice imaging (SMS) described herein with respect to certain embodiments. The computer 200 can include a data store 220 for storing data that may include imaging-related data 222 such as acquired data from the implementation of magnetic resonance imaging in accordance with various embodiments of the disclosed technology.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology.

The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more example embodiments and implementations discussed above. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202. Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

EXAMPLE IMPLEMENTATIONS AND CORRESPONDING RESULTS

The following description includes discussion of example implementations of certain aspects and embodiments of the present disclosure, and corresponding results. Some experimental data are presented herein for purposes of illustration and should not be construed as limiting the scope of the present disclosure in any way or excluding any alternative or additional embodiments.

Example 1

The following describes one example implementation of aspects of the present disclosure in accordance with some embodiments, in which a spiral SMS acquisition and CS reconstruction achieve multi-slice whole heart coverage (6-9 slices) which utilizes simultaneous excitation of 2-4 slices to maximize the data sampling time for each slice, improving SNR efficiency as compared to prior interleaved highly-accelerated approaches.

Methods

Theory

When multiple slices are excited simultaneously, the raw k-space signal can be expressed in a generalized form as:

$$S_{mb} = \sum_{j=1}^{nSlc} S_j * e^{i\Phi_j}$$

Where the $S_{mb}$ is the vector representing multiple slices excitation raw k-space signal, $S_j$ is raw k-space signal of the $j^{th}$ slice, nSlc is the total number of slices excited and $e^{i\Phi_j}$ is the phase modulation for the k-space of the $j^{th}$ slice.

Without phase modulation ($\Phi_j=0$), the resulted MB signal would be the superposition of the signals from all slices. Typically, a SENSE (sensitivity encoding) or GRAPPA (generalized autocalibrating partially parallel acquisitions) approach is used to separate the images by directly or indirectly exploring variation in coil sensitivities in the through-slice direction. However, the direct overlap of the images results in a high g-factor for high MB factors. To reduce the g-factor, the concept of CAIPIRINHA ([1]) was introduced. This technique modulates the phase of the rf excitation ($\Phi_j=[0\ \pi\ 0\ \pi\ \ldots]$) of each slice to induce a linear phase shift along phase encoding direction to prevent direct overlap of the reconstructed images from each slice. This linear phase shift in the k-space data results in a position shift in the image domain reducing direct overlap between slices resulting in lower g-factors and improved image reconstruction quality.

For non-Cartesian data acquisition, the phase-shifting approach does not provide a linear position shift, but rather enables cancellation of data from different slices. By carefully choosing a sampling strategy and excitation phase modulation scheme, signals from the desired slice add coherently, while signals from other slices destructively interfere resulting in an aliasing pattern, which can be removed by parallel imaging and/or compressed sensing reconstruction. For spiral trajectories, the density can be modified to fully-sample or over-sample the k-space center, enabling a trade-off between sampling efficiency and signal cancellation for each slice. Higher MB factors need a phase cycling strategy for each slice such that the contribution from the other slices is minimized when a single slice is being reconstructed. An orthogonal set of phase cycling angles following a Hadamard pattern ([2]), which is orthonormal, can achieve this desired signal cancellation. This strategy requires $2^{(MB-1)}$ interleaves. For an 8 spiral interleaved design, the phase modulation for each slice up to MB factor of 4 is given as follows:

$\Phi_1=[0\ 0\ 0\ 0\ 0\ 0\ 0\ 0]$ $\Phi_2=[0\ \pi\ 0\ \pi\ 0\ \pi\ 0\ \pi]$ $\Phi_3=[0\ 0\ \pi\ \pi\ 0\ 0\ \pi\ \pi]$ $\Phi_4=[0\ 0\ 0\ 0\ \pi\ \pi\ \pi\ \pi]$

Figure 2:
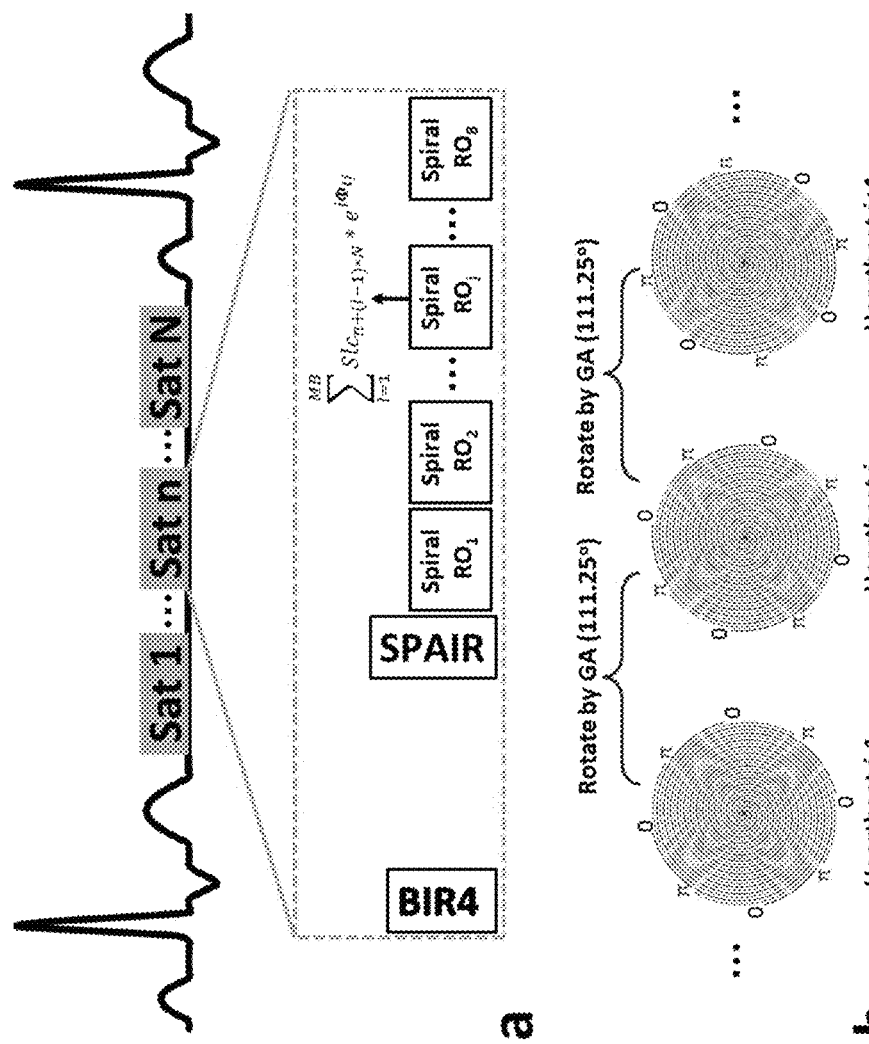
FIG. 2 shows a schematic of an SMS spiral perfusion pulse sequence in accordance with one embodiment of the present disclosure.

FIG. 1 shows the effect of the phase modulation scheme on the signal from each slice for an example of phase modulation of 8 spiral interleaves at MB=1, 2, 3 and 4. FIG. 1 at (a) shows images from the 4 different slice locations. After phase modulation (b) the contribution of the phase modulated signal for the images for each slice is shown in column (c). Slice 1 (red) has no phase modulation and is thus unchanged from column (a). The images from the slices 2-4 following excitation phase modulation show minimal signal from the heart, and demonstrate a characteristic aliasing pattern depending of the phase modulation pattern for each slice. Column (d) shows the effect for slice 1 of adding the data from the modulated slices for MB factors 2-4. Columns e-g show the raw image data from slices 2-4 at the various multiband factors. In all cases the residual signal from the modulated slices appears as an incoherent noise artifact with an increasing amount of residual aliasing artifacts as the MB factor is increased. Without any temporal variation of the sampling pattern, this aliasing pattern would be coherent and could be reconstructed using a "slice-GRAPPA" like approach. However, by varying the sampling pattern for each heart beat by the golden-angle as shown in FIG. 2 at (b), the residual aliasing pattern becomes incoherent in time and amenable to reconstruction using compressed sensing (CS). In accordance with some embodiments of the present disclosure, the multiple-slices can be jointly reconstructed across the time series using an SMS-parallel imaging and CS approach that the inventors have named non-Cartesian SMS-L1-SPIRiT, as further described below.

Figure 10:
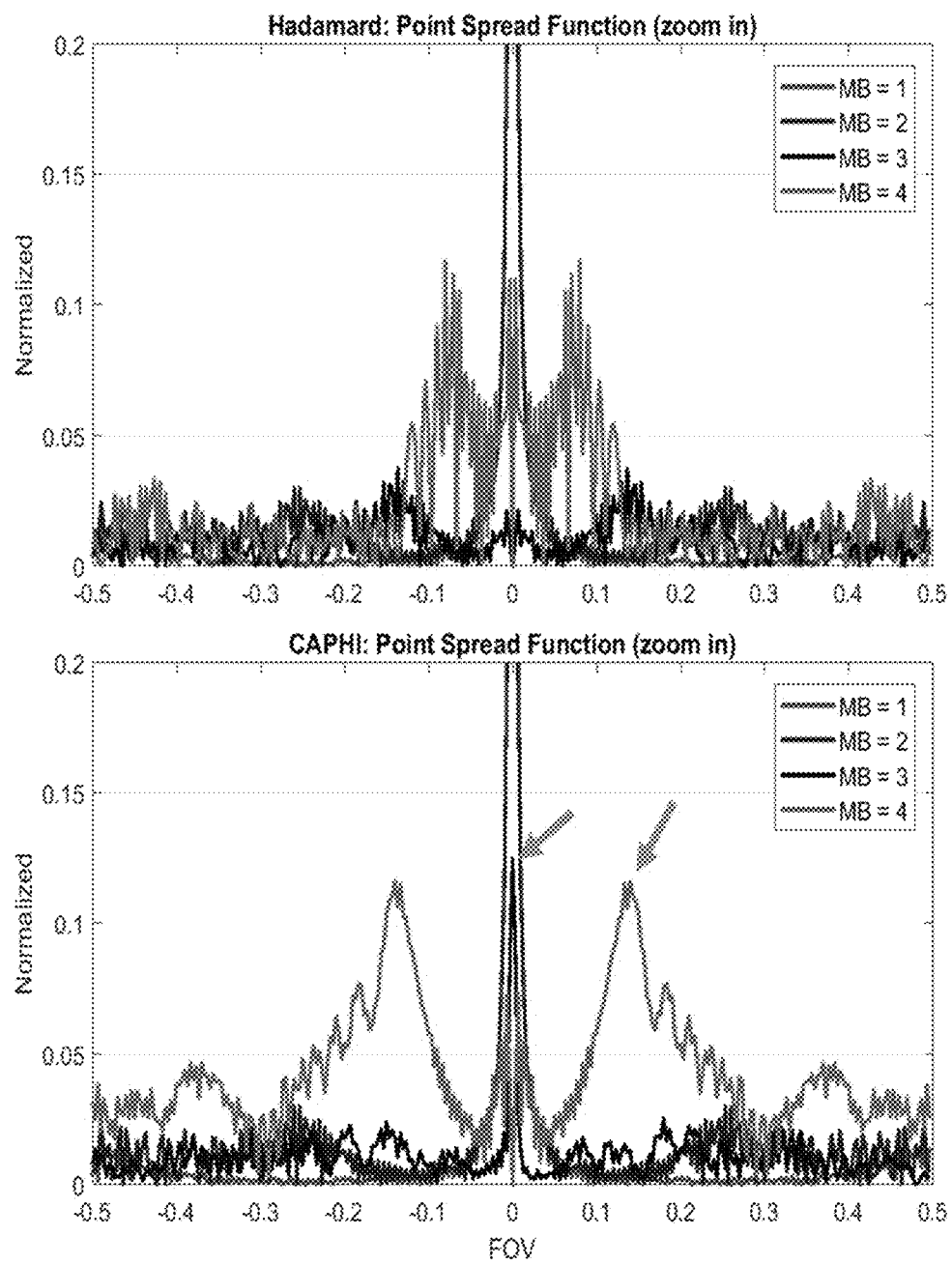
FIG. 10 shows a comparison of the point spread functions (PSFs) for a Hadamard (top) and CAIPIRINHA (bottom) sampling pattern for an 8 interleaf spiral acquisition at MB factors of 2-4.

For an 8-interleaf spiral acquisition, the Hadamard strategy was chosen over the standard CAIPIRINHA approach, as it can achieve better suppression of signal from the phase modulated slices for all MB factors between 1 and 4. FIG. 10 shows a comparison of the PSFs for the Hadamard (top) and CAIPIRINHA (bottom) sampling pattern. For MB=2 the PSF is the same for CAIPIRINHA or Hadamard, since they use the same phase modulation scheme. However, for MB=3, the CAIPIRINHA scheme does not achieve the same level of suppression of the main-lobes of the other two slices as compared to the Hadamard strategy. CAIPIRINHA achieved better suppression of signal when the number of interleaves is a multiple of the MB factor. For MB=4, both Hadamard and CAIPIRINHA achieve good main lobe energy cancellation, however the side lobes energy distribution from CAIPIRINHA is slightly more coherent compared with the Hadamard scheme. For CAIPIRINHA, two of the slices have similar aliasing patterns, resulting in more coherent side-lobes of the PSF. In summary, for higher multi-band factors with a $2^n-1$ number of spiral interleaves, the Hadamard scheme results in improved incoherence of the point spread function.

Pulse Sequence

The SMS spiral perfusion pulse sequence in accordance with an embodiment of the present disclosure is shown schematically in FIG. 2 at (a). A non-selective saturation with an adiabatic BIR-4 pulse is used for T1-weighted preparation. A spectrally selective adiabatic fat-saturation pulse is applied before data acquisition. An 8 interleaved spiral trajectory was used with the following design parameters: 6 ms readout per spiral interleave with linear variable density starting density of 1.2× Nyquist to ending density of 0.4× Nyquist. Given the nature of variable density spirals where the acceleration rate varies during the trajectory by design, the effective acceleration rate is defined as the corresponding constant acceleration factor required for a uniform density spiral trajectory to achieve the same desired FOV and maximum k-space radius (nominal spatial resolution) with the same number of interleaves and readout duration per interleave. Therefore, the effective acceleration rate for this VD (variable density) spiral is 1.25 fold. Other sequence parameters included: FOV 340 mm, TE 1.0 ms, TR 8 ms, SRT 80 ms, FA 26°, with 10 mm thickness, 2 mm in-plane resolution, and MB factors from 1-4.

The multiband RF pulse was designed by the summation of single band RF pulse with different phase modulation for each slice. The single band RF pulse is a 1 ms sinc-shaped pulse with time band product of 5.6. The peak amplitude of the multiband RF pulse and the total power in the pulse was confirmed to not exceed specific absorption rate (SAR) limits. The excitation phase of each slice in the SMS acquisition was modulated using the previously described Hadamard phase cycling scheme to achieve MB factors of 1-4. One to 4 slices are acquired in each SR block, and SR blocks are repeated until all the slices are imaged. To achieve temporal incoherence, the excitation phase modulation angle was incremented by the golden-angle between heartbeats as shown in FIG. 2 at (b) using MB factor of 2 as an example. Full heart coverage can be achieved with MB factor 2, 3, and 4 with 4, 3, or 2 saturation blocks respectively.

A pre-scan, consisting of images acquired at each slice location (i.e., without SMS) without magnetization preparation, was acquired during a separate 10 heartbeat breath hold to derive the calibration kernel for SMS reconstruction. The k-space trajectory was the same as that used for acquisition of the perfusion data. The sequence parameters included: FOV 340 mm, TE 1.0 ms, TR 8 ms, FA 10°, with 10 mm thickness, 2 mm in-plane resolution.

Reconstruction

In accordance with some embodiments of the present disclosure, the perfusion images were reconstructed using the following SMS-L1-SPIRiT technique:

$$\operatorname*{argmin}_{x} \|\Phi F_u x - y\|^2 + \lambda_1 \|(G-I)x\|^2 + \lambda_2 \|\Psi_t x\|_1$$

where $F_u$ is a Non-uniform Fourier operator which transfers the data from the image domain to the spiral k-space domain, G is an image-space SPIRiT (iterative self-consistent parallel imaging reconstruction) ([3]) operator that represents the k-space self-consistency convolutions in the image domain, $\Psi_t$ is the finite time difference transform that operates on each individual coil separately to achieve sparsity in the temporal domain of image time series, $\Phi$ is the operator describing the phase modulation pattern needed to coherently select the signal from each slice from the SMS data, and $\lambda_1$ and $\lambda_2$ are parameters that balance the data acquisition consistency with calibration consistency and sparsity. The calibration kernel is derived from the pre-scan proton density images described in the pulse sequence section.

Human Studies

In accordance with one implementation, forty patients undergoing clinically ordered CMR studies with gadolinium (Gd)-based contrast agents were included in this study. The indications for the clinical CMR studies included evaluation of myocardial viability (N=8), myocardial infarction (N=5), left ventricular dysfunction (N=4), heart failure (N=1), myocarditis (N=1), pre-ablation (N=1), pericardial disease (N=2), arrhythmias (premature ventricular contractions/ventricular tachycardia) (N=3), cardiac sarcoid (N=3), hypertrophic cardiomyopathy (N=11) and right ventricular enlargement (N=1). Imaging was performed on a 1.5T MRI scanner (MAGNETOM Aera, Siemens Healthineers, Erlangen, Germany). Perfusion imaging was performed using 0.075 mmol/kg of Gd-DTPA (Bayer AG, Leverkusen, Germany) injected intravenously at a rate of 4 mL/s followed by 25 mL of saline flush at 4 mL/s. The subjects were asked to hold their breath as long as possible followed by shallow breathing during the acquisition of perfusion images over 50-60 heartbeats. A 34-channel cardiac phased-array receiver coil was used for signal reception. 10 studies were performed at each MB factor. 4 slices, 6 slices, 9 slices, and 8 slices were acquired for MB factors of 1-4 respectively. All patients underwent late gadolinium enhancement (LGE) imaging with phase-sensitive inversion recovery (PSIR) as part of the standard clinical CMR protocol. The sequence parameters of PSIR included: FOV 320-380 by 260-300 mm with 75% phase resolution, matrix size 256×156, in-plane spatial resolution between 1.25 and 1.5 mm, inversion time in the range of 320 to 400 ms, slice thickness 8 mm, TE 3.2 ms, FA 25o, breath-hold and ECG-trigged for 16 heart beats.

Image Analysis

To validate the reconstruction performance, data acquired with MB=1 was used to retrospectively simulate acquisition and reconstruction for MB factors of 2-4. The retrospectively reconstructed images were assessed quantitatively as compared to the MB=1 images as a gold-standard using normalized root mean square error (NRMSE) and the structural similarity index (SSIM) measured in a manually drew region of interest only containing the heart. The NRMSE and SSIM was analyzed by two-way analysis of variance (ANOVA) with subject as the blocking factor factorial and a P-value<0.05 was considered significant.

Perfusion images for MB factors of 1, 2, 3, and 4 were first reconstructed by SMS-L1-SPIRiT. The reconstruction parameters $\lambda_1=0.02$ and $\lambda_2=0.05$ were chosen based on the L-curve analysis, and the parameters were fixed for all datasets. Next, dynamic perfusion images from 3 slice locations (basal, mid, and apical) were randomly selected from each patient study for blind grading on a 5-point scale (5=excellent, 1=poor) by two cardiologists for image quality assessment. Image quality scores between MB factors were analyzed using the Kruskal-Wallis test.

Results

Figure 3:
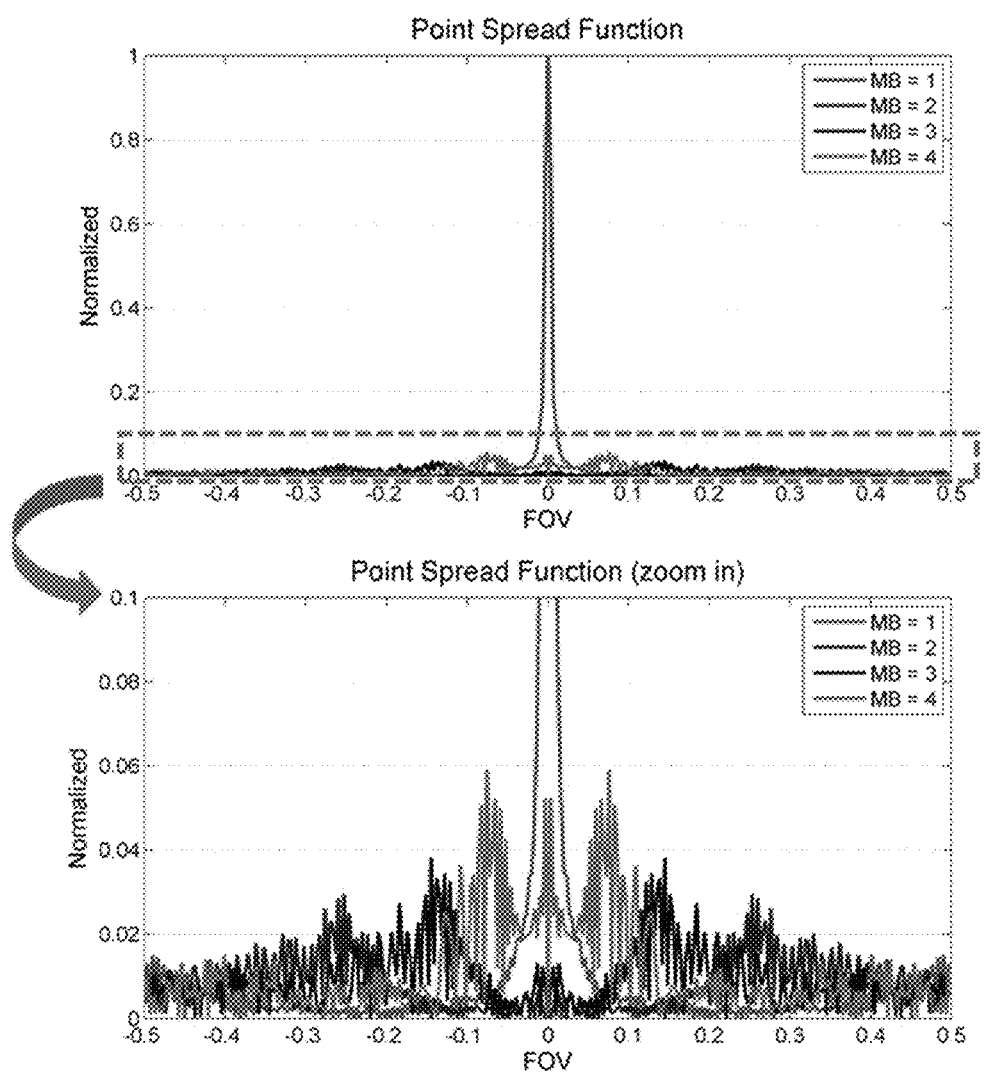
FIG. 3 shows a point spread function (PSF) analysis of the MB=1, and the interference pattern added by the additional excited slices for MB=2, 3 and 4 acquisition. The majority of the main lobe energy is cancelled for MB slices 2-4 due the phase sampling scheme. The side lobe amplitude is only 6% of the main lobe amplitude for the MB=1 PSF, and has an incoherent pattern suitable for SMS-L1-SPIRiT reconstruction according to some embodiments of the present disclosure.
Figure 4:
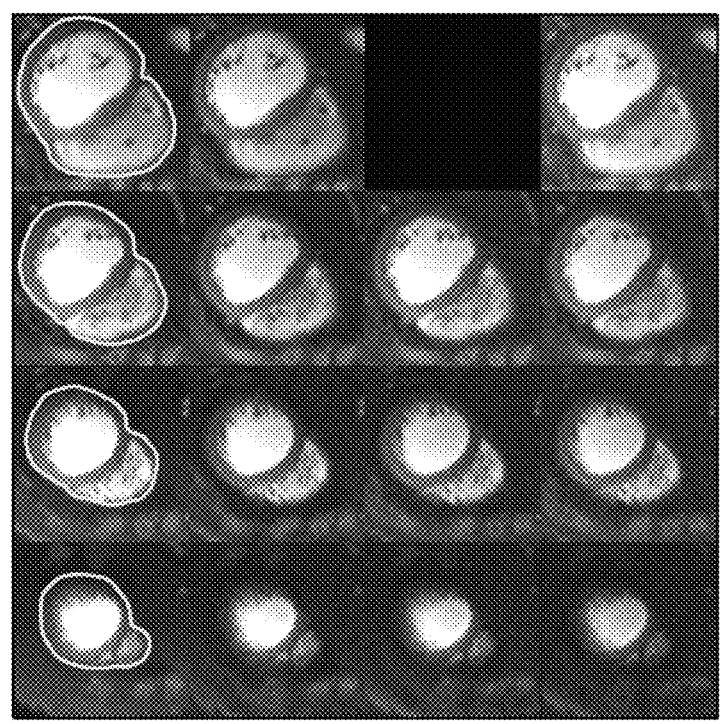
FIG. 4 shows a retrospective SMS reconstruction, where the perfusion images in the top row are collected without SMS (i.e., MB=1) and reconstructed with L1-SPIRiT to serve as the "gold-standard". The subsequent rows show images with simulated MB factors of 2 to 4 reconstructed using SMS-L1-SPIRiT in accordance with some embodiments of the present disclosure. This reconstruction technique has minimal residual aliasing artifacts, even at MB=4. The perfusion images simulated at MB 2 to 4 visually have image quality comparable to the ground truth MB 1 reconstruction.
Figure 5:
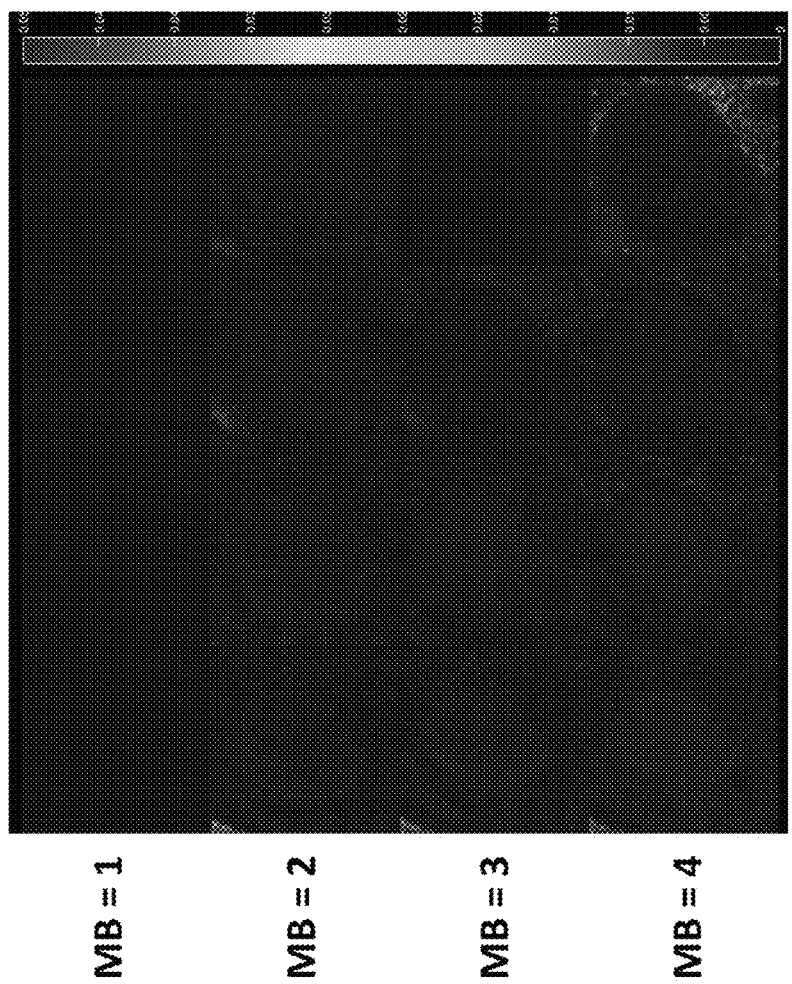
FIG. 5 shows retrospective normalized root mean square error (NRMSE) maps from one subject showing the corresponding residual error as compared with gold-standard images.

FIG. 3 shows the point spread function (PSF) of the MB=1, and the interference pattern added by the additional excited slices for MB=2, 3 and 4 acquisition. The majority of the main lobe energy was cancelled for MB slices 2-4 due the phase sampling scheme, and the side lobe amplitude were 6% of the MB 1 main lobe amplitude of MB 1 with an incoherent pattern suitable for SMS-L1-SPIRiT reconstruction. FIG. 4 demonstrates example perfusion images from one case from the retrospective experiment. The images in the top row were collected without SMS (i.e., MB=1) and reconstructed with L1-SPIRiT to serve as the "gold-standard". The subsequent rows show images with simulated MB factors of 2 to 4 reconstructed with the SMS-L1-SPIRiT pipeline. This reconstruction technique had minimal residual aliasing artifacts even at the highest MB factor of 4. The perfusion images simulated at MB 2 to 4 visually have image quality comparable to the ground truth MB 1 reconstruction. FIG. 5 shows the NRMSE maps from the same subject showing the corresponding residual error as compared with gold-standard images for MB factors of 2 to 4.

Figure 6:
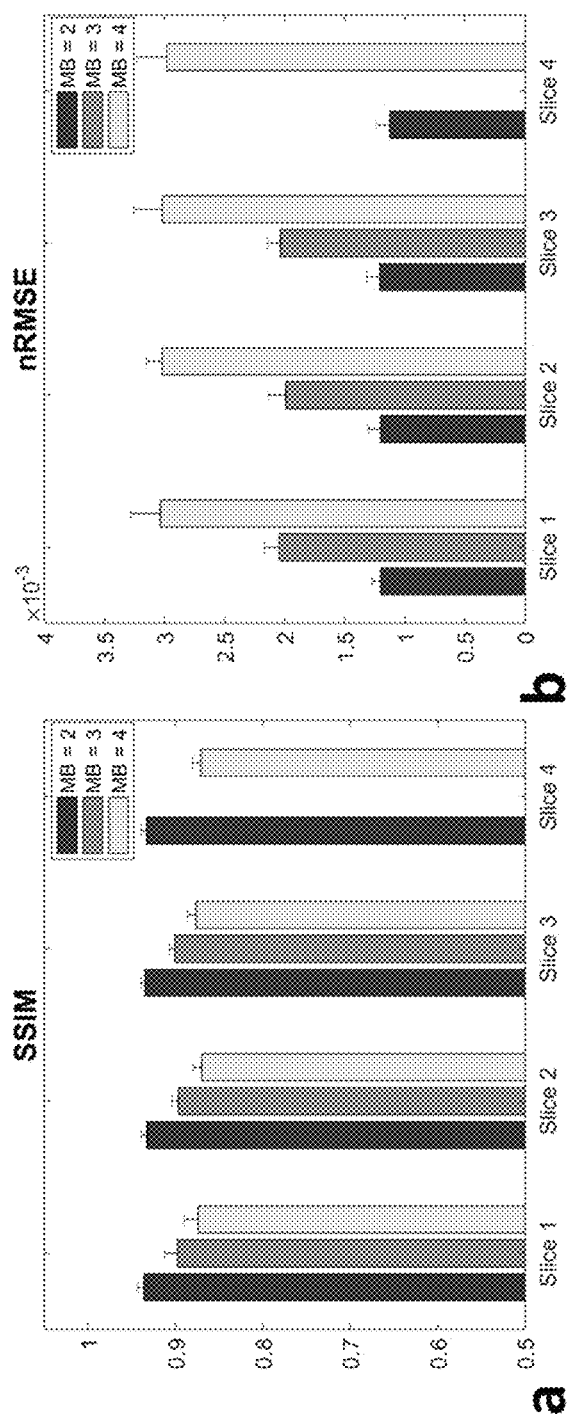
FIG. 6 shows quantitative analysis of structural similarity index[32] (SSIM) (a) and NRMSE (b) from the retrospective experiments of different MB factors at all slice locations. Increasing the MB factor raised NRMSE while lowering SSIM values. However, the NRMSE from MB factors 2 to 4 at all slice locations is smaller than 0.5% of the ground truth signal, implying good reconstruction performance.
Figure 7:
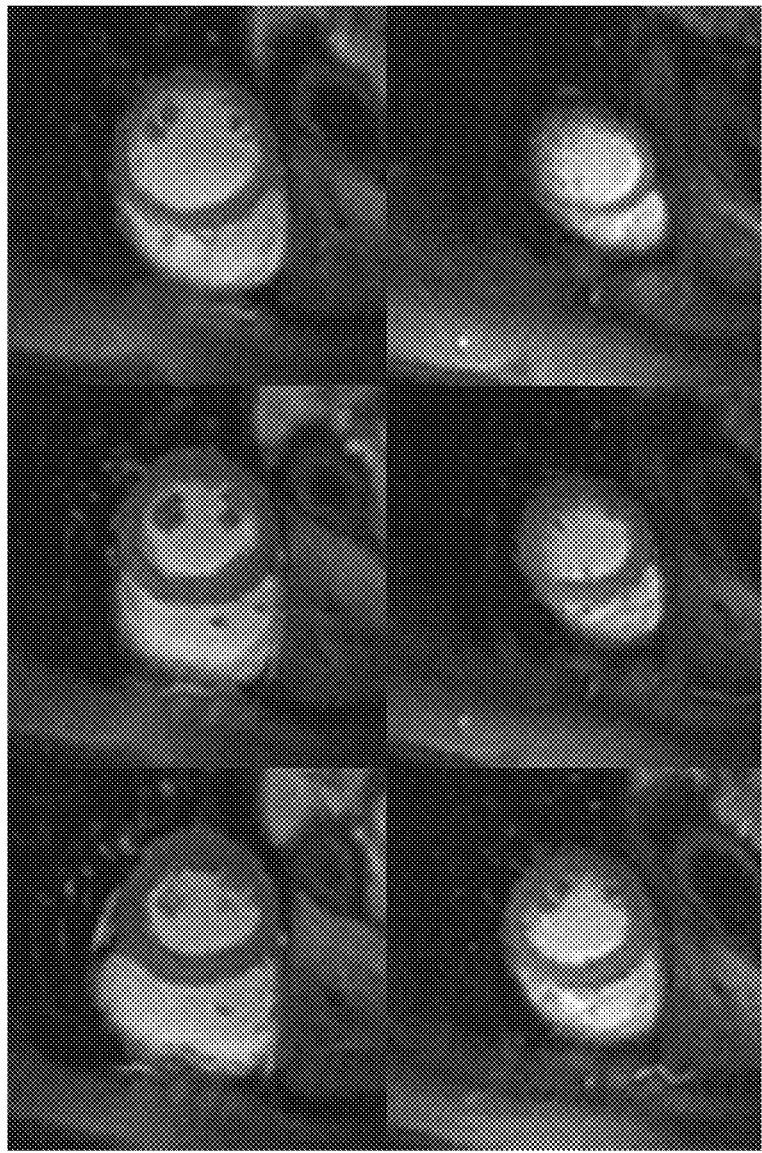
FIG. 7 shows perfusion images from a patient (female, 48 years old, evaluated for hypertrophic cardiomyopathy) acquired with MB=2 and 6 slices per heartbeat at a single time point during first-pass of contrast.
Figure 8:
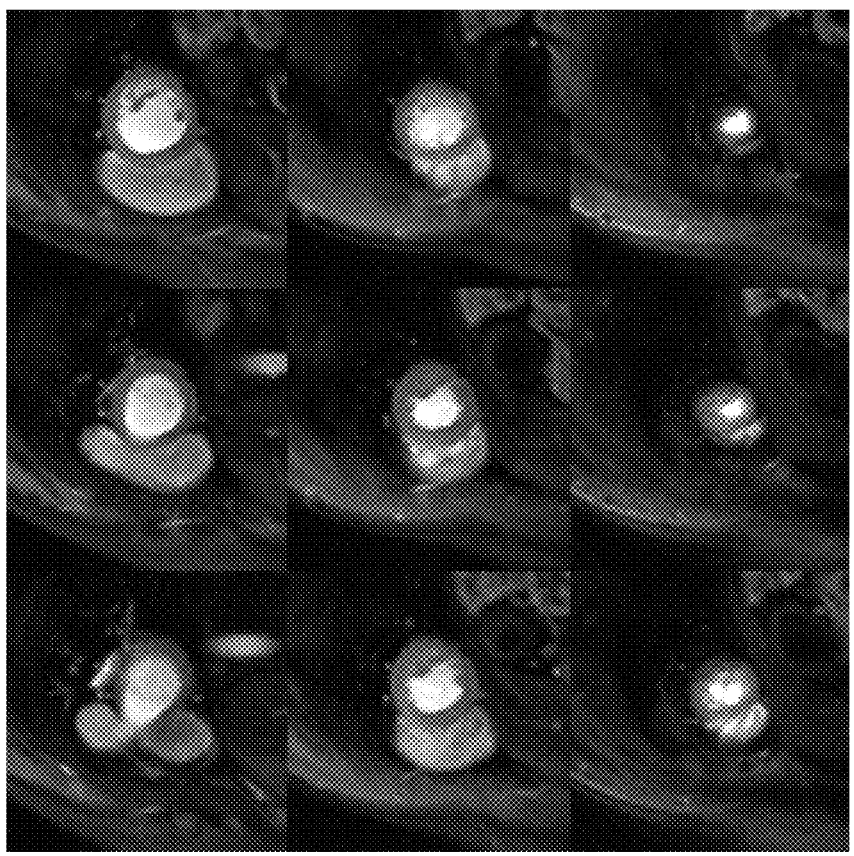
FIG. 8 shows perfusion images from a patient (female, 40 years old, evaluated for LV dysfunction) acquired with MB=3 and 9 slices per heartbeat at a single time point during first-pass of contrast.
Figure 9:
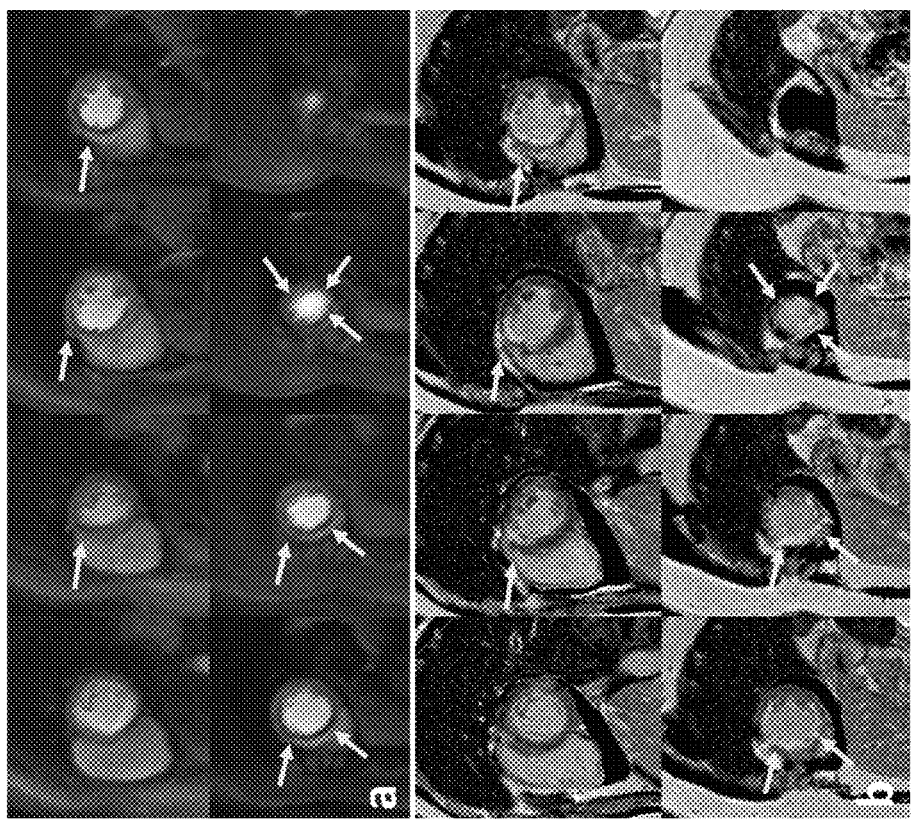
FIG. 9 shows perfusion images from an ST-elevation myocardial infarction (STEMI) patient (female, 48 years old) at an MB=4 with 8 slices per heartbeat. Even at a higher MB factor, the perfusion images (a) clearly delineated a perfusion abnormality corresponding with the infarction on the late gadolinium enhanced (LGE) images (b).

FIG. 6 shows the quantitative analysis of NRMSE and SSIM from the retrospective experiments of different MB factors at all slice locations. Increasing the MB factor results in significantly higher NRMSE and lower SSIM values. However, the NRMSE from MB factors 2 to 4 at all slice locations is smaller than 0.5% of the ground truth signal, implying good reconstruction performance. FIG. 7 shows perfusion images from a patient acquired with MB=2 and 6 slices per heartbeat at a single time point during first-pass of contrast. FIG. 8 shows perfusion images acquired with MB=3 and 9 slices per heartbeat. Images acquired with both MB=2 and MB=3 demonstrate high image quality while maintaining the same spatial-temporal resolution as the single-excitation technique. FIG. 9 demonstrates perfusion images from an ST-elevation myocardial infarction (STEMI) patient at an MB=4 with 8 slices per heartbeat. Even at this high MB factor, the images (a) clearly delineated a perfusion abnormality with a location corresponding to the infarction on the late gadolinium enhanced (LGE) images (b).

The image quality scores are 4.2±0.5 (MB=2), 4.3±0.5 (MB=3) and 4.5±0.3 (MB=4) from cardiologist one, 4.4±0.5 (MB=2), 4.2±0.5 (MB=3) and 4.2±0.8 (MB=4) from cardiologist two, with no significant quality difference in image quality between MB factors (p=0.40 for cardiologist one and p=0.58 for cardiologist two).

Discussion

The SMS spiral perfusion sequence with MB factors 2 to 4 enabled high quality and high spatial-temporal resolution perfusion images with whole heart coverage without additional scan time. In Cartesian SMS perfusion imaging using CAIPIRINHA and a parallel imaging reconstruction, phase modulation is used to shift the spatial location of the images from the different slice locations. At higher MB factors, there is significant reduction in g-factor resulting in reconstructed images with reduced image quality and spatially varying noise amplification. For the non-Cartesian SMS approach using a phase modulation scheme to cancel signal from other slices, the aliasing pattern from the different slice locations appear as an incoherent swirling artifact. By rotating the spiral sampling pattern in time by the golden angle, temporal incoherence of the aliasing artifacts is also achieved. These two factors favor an CS reconstruction such as the SMS-L1-SPIRiT approach in accordance with embodiments of the present disclosure. Blinded visual analysis showed high image quality across MB factors 2-4 likely due to the absence of coherent aliasing artifacts. From the quantitative analysis, it is shown that the image degradation at higher MB factors for this approach appears as noise enhancement. The high SNR efficiency of the spiral acquisition combined with the incoherent spatial and temporal aliasing artifacts likely explain the differences between the results and the prior Cartesian SMS results for imaging at high MB factors. Finite-difference in time was chosen as the sparsity constrained term, as artifacts due to respiratory motion, which usually occur near the end of the breath-hold, tend to be localized to only this portion of the data acquisition. The inventors have recently demonstrated a technique based on a simple rigid-registration of the heart region which further improves robustness of the CS reconstruction to motion ([4]).

Retrospective reconstruction experiments based on MB=1 clinical datasets showed that as the MB factor increased, the NRMSE also increased. This is due to the fact that more aliasing energy was added from the additional slices, and the constrained reconstruction did not fully recover the images from high MB factors. However, the average NRMSE from all the datasets at all MB factors was still below 0.5% in the heart ROI (region of interest), with the majority of the increased NRMSE in the lung region resulting in visually similar image quality. The retrospective experiments also demonstrated that the chest wall and body fat contribute to the majority of high-energy aliasing artifacts, which are not completely removed by the phase-modulation strategy.

Improved fat suppression or spectral-spatial water-excitation pulses ([5]) may more effectively suppress the signal from chest fat, improving the performance of the SMS spiral perfusion technique. In addition, outer volume suppression ([6]), which has been demonstrated for spiral perfusion imaging, can be incorporated into this SMS spiral perfusion sequence to further suppress the signals outside the heart to achieve more benign and incoherent aliasing pattern.

In vivo evaluation in patients undergoing CMR studies demonstrated that the disclosed spiral SMS perfusion technique resulted in high quality images at MB factors of 2-4, which had similar image quality to single band variable density spiral perfusion images. The scan efficiency is greatly improved by SMS, which enabled whole heart coverage with the same temporal footprint as in the previously validated 3-slice perfusion technique. The disclosed SMS spiral perfusion sequence can support heart rate up to 100 BPM (MB=2), 133 BPM (MB=3) and 200 BPM (MB=4) with minimal 8 slice locations to cover the whole ventricle. Despite the similar image qualities from the in vivo cases among different MB factors, the retrospective study still demonstrated with the higher MB factor, the potential image quality would be reduced. The recommendation for practical selection of MB factors in clinical cases should base on patient's heart rate to choose the lower MB factor with the desired ventricle coverage. Whole heart coverage by utilizing higher in-plane accelerated spirals with a slice-interleaved acquisition has previously been demonstrated. In the slice interleaved approach, spiral interleaves are collected by alternating the slice location which is selectively excited; in this approach, data is only being acquired from each location for half of the total acquisition time for the two slices. Without other changes in the sequence this results in a SQRT(2) loss of SNR for each slice position due to the reduction in sampling time. Furthermore, the slice interleaved approach required a higher in-plane acceleration factor (5×) to achieve the same resolution as the SMS MB=2 acquisition which only required a 1.25× in-plane acceleration factor. The reduction of in-plane acceleration may improve L1-SPIRiT reconstruction, and the longer acquisition time for each slice improves the underlying SNR of the raw data. If the MB factor is considered as an additional acceleration factor, the total acceleration for SMS acquisition with MB 2 to 4 are 2.5, 3.75 and 5× respectively. The above factors create a practical limitation of about 2 slices per saturation for a slice interleaved spiral acquisition, whereas with SMS, 3-4 slices can be acquired simultaneously following a single saturation pulse. Furthermore, the slice interleaved approach required a higher in-plane acceleration factor (5×) to achieve the same resolution as the SMS MB=2 acquisition which only required a 1.25× in-plane acceleration factor. The reduction of in-plane acceleration may improve L1-SPIRiT reconstruction, and the longer acquisition time for each slice improves the underlying SNR of the raw data. If the MB factor is considered as an additional acceleration factor, the total acceleration for SMS acquisition with MB 2 to 4 are 2.5, 3.75 and 5× respectively. The fundamental limit on the multi-band factor that can be achieved using the disclosed spiral-SMS approach is not currently known. This will likely be a function of the intrinsic SNR of the raw data, the incoherence of the PSF and the amount of residual aliasing artifact, as manifested by an increase in NRMSE, which results in clinically acceptable images. For myocardial perfusion imaging, typically about 8-10 slices are needed to cover the whole heart. Given that the slices are typically sliced by one slice dimension to avoid cross-talk between slices, practically MB factors above 4 (to perhaps 5) may not be necessary for this implementation to achieve whole heart coverage.

The spiral SMS perfusion pulse sequence according to embodiments of the present disclosure presented herein can be further extended to 3T to achieve higher in-plane spatial resolution with good image quality, which can provide a tool to assess regional difference in the perfusion of the subendo and subepi myocardium.

The disclosed spiral design was based on prior perfusion clinical experience with linear variable density spiral trajectories ([7]), which have benign undersampling aliasing artifacts. Additional optimization of the spiral trajectories and temporal sampling pattern may further improve the performance of this technique. A goal of this study was to evaluate whether directly accelerating the acquisition of spiral perfusion imaging is feasible with SMS MB factors of 2-4. The inventors chose this temporal sampling strategy so that the residual aliasing artifacts resulting from the Hadamard phase-cycling strategy would be incoherent in time and amenable to a temporal CS constraint. Further optimization of the temporal sampling pattern and phase cycling strategy may also improve image reconstruction.

In conclusion, this example implementation shows the successful application of an SMS spiral perfusion at MB factor 2, 3 and 4 in a clinical setting. Due to the increased sampling efficiency of SMS, whole heart coverage was achieved with high image quality without the need for interleaving slices or significantly shortening the readout time for each slice. Further validation may be performed in patients undergoing vasodilator stress CMR.

Example 2

The following describes another example implementation of aspects of the present disclosure in accordance with some embodiments. In accordance with this example implementation, a spiral pulse sequence achieves high spatial resolution of 1.25 mm at 3T.

Methods

Figure 11:
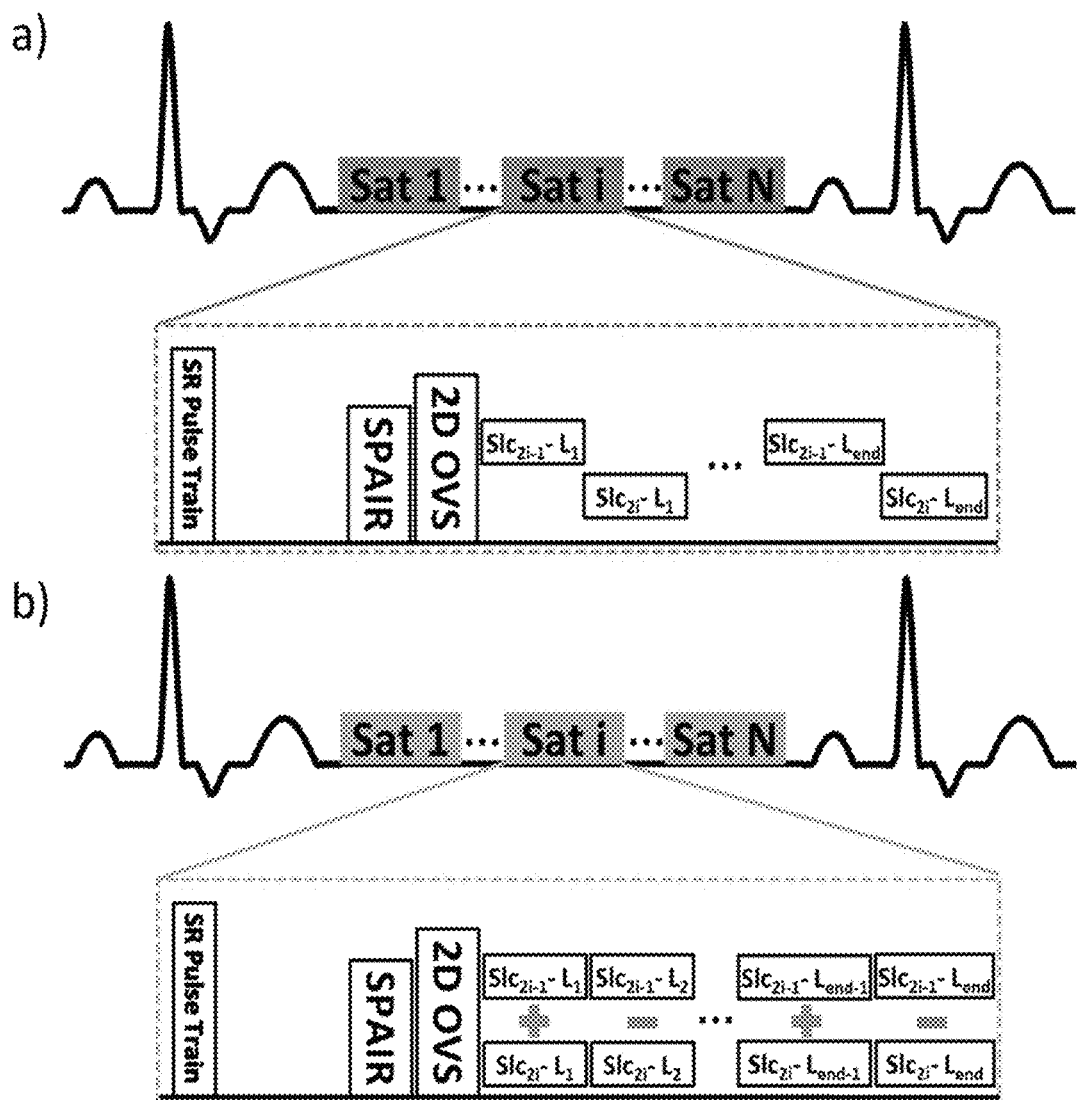
FIG. 11 shows pulse sequence schematics for (a) outer-volume suppression (OVS) with interleaved acquisition and (b) OVS with SMS techniques.

Two different pulse sequences were evaluated in this study, including an interleaved acquisition of two slices per saturation recovery (SR) block, and SMS with a multiband factor of 2 per SR. An optimized 5 hard-pulse SR was used to reduce SAR in 3T. Both sequences utilized an OVS module containing a BIR-4 tip-down pulse, a 2D spiral tip-back pulse, and a spoiler to crush residual signal. The sequence schematic is shown in FIG. 11 and detailed parameters are listed in Table 1. Resting first-pass perfusion was performed using both sequences with a 0.075 mmol/kg Gd-DTPA bolus, separated by 20 min contrast washout time, in 9 healthy subjects on a 3T Prisma Siemens scanner. The images were reconstructed by L1-SPIRIT or SMS-L1-SPIRiT using finite temporal difference as the sparsity transform. Image quality of both sequences were graded on a 5-point scale (5 excellent, 1 poor) by an experienced cardiologist.

TABLE 1

Pulse sequence parameters

| | Sequence 1 (OVS + interleaved) | Sequence 2 (OVS + SMS) |
|---|---|---|
| FOV (mm) | 170 | 170 |
| Spatial resolution (mm) | 1.25 | 1.25 |

TABLE 1-continued

Pulse sequence parameters

|  | Sequence 1 (OVS + interleaved) | Sequence 2 (OVS + SMS) |
| --- | --- | --- |
| Spiral interleaves | 4 | 8 |
| Spiral readout per interleave (ms) | 5 | 5 |
| # of slices acquired per SR | 2 | 2 |
| Starting density (Nyquist) | 1 | 2 |
| Ending density (Nyquist) | 0.16 (6 fold) | 0.33 (3 fold) |
| Temporal resolution (ms) | 54.6 | 62.4 |
| inversion time (ms) | 120 | 120 |
| Flip angle (degree) | 26 | 18 |
| # of Slices | 6-8 | 6-8 |

Results

Figure 12:
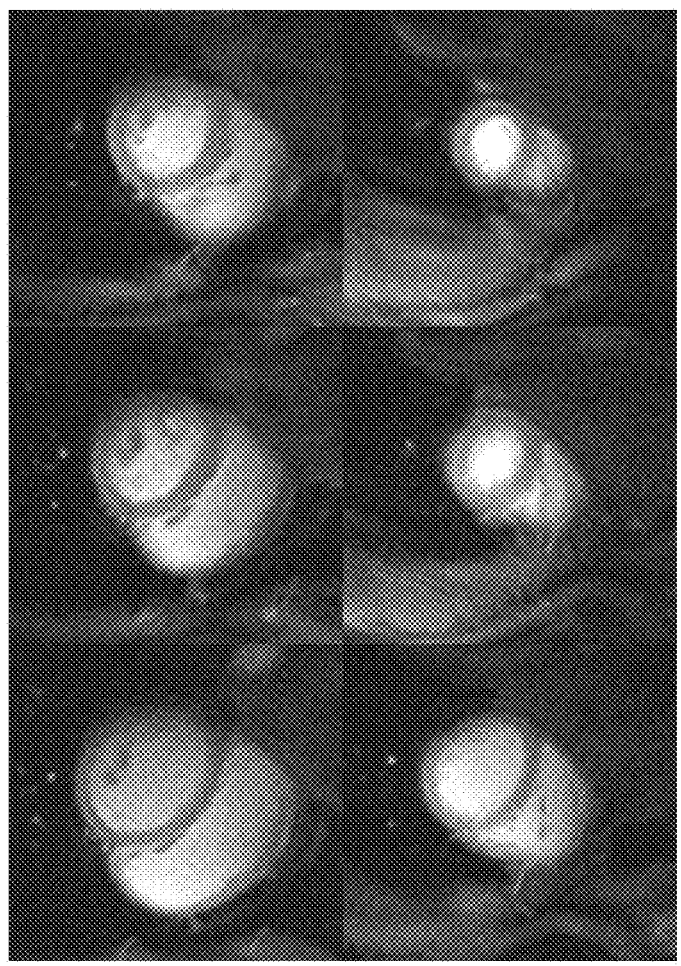
FIG. 12 shows spiral perfusion images acquired with 1.25 mm spatial resolution using OVS and interleaved acquisition pulse sequences.
Figure 13:
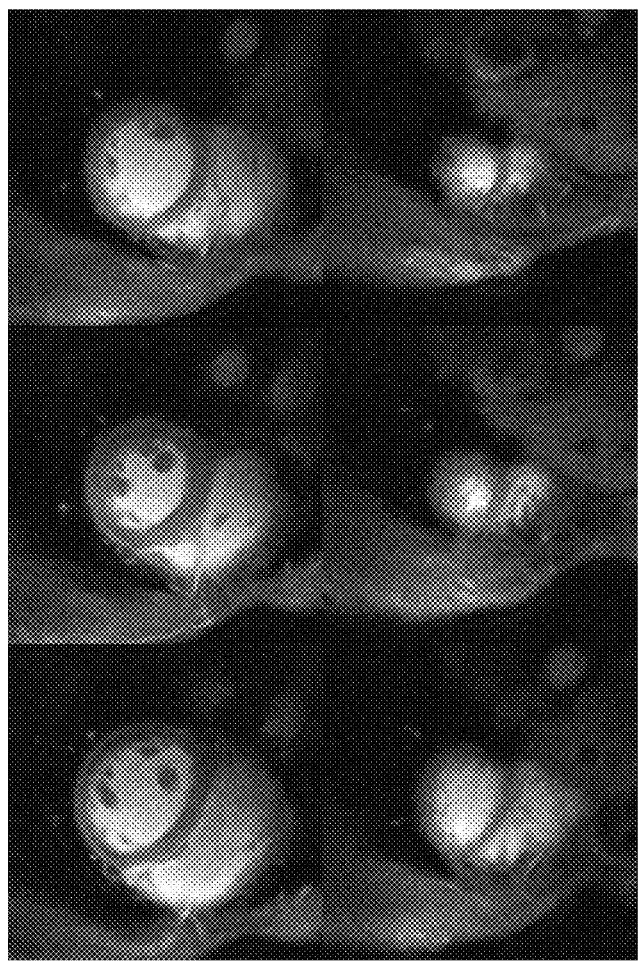
FIG. 13 shows spiral perfusion images acquired with 1.25 mm spatial resolution using OVS and SMS techniques pulse sequences.

FIG. 12 shows an example of 6 slice perfusion images with 1.25 mm resolution of the OVS+interleaved sequence. FIG. 13 shows another example of high spatial resolution perfusion images using an OVS SMS sequence. The average image scores of the interleaved and SMS sequences were 3.3±0.5 and 2.9±0.3 respectively (p=0.01). There was some signal dropout in the inferior wall due to off-resonance effects, which may be mitigated by further shortening the spiral readout durations.

Conclusion

In accordance with the implementations described for this example, an ultra-high resolution spiral perfusion sequence was applied using OVS and SMS techniques. High resolution, whole heart perfusion may be used to quantify regional of the subendo and subepi myocardium. Further validation may be done in patients undergoing adenosine stress CMR.

Example 3

The following describes another example implementation of aspects of the present disclosure in accordance with some embodiments. This example describes a spiral pulse sequence with slice-interleaved or simultaneous multi-slice (SMS) acquisition without OVS to achieve high quality ultra-high 1.25 mm resolution perfusion imaging. The sequences were tested in healthy volunteers.

Methods

Figure 14:
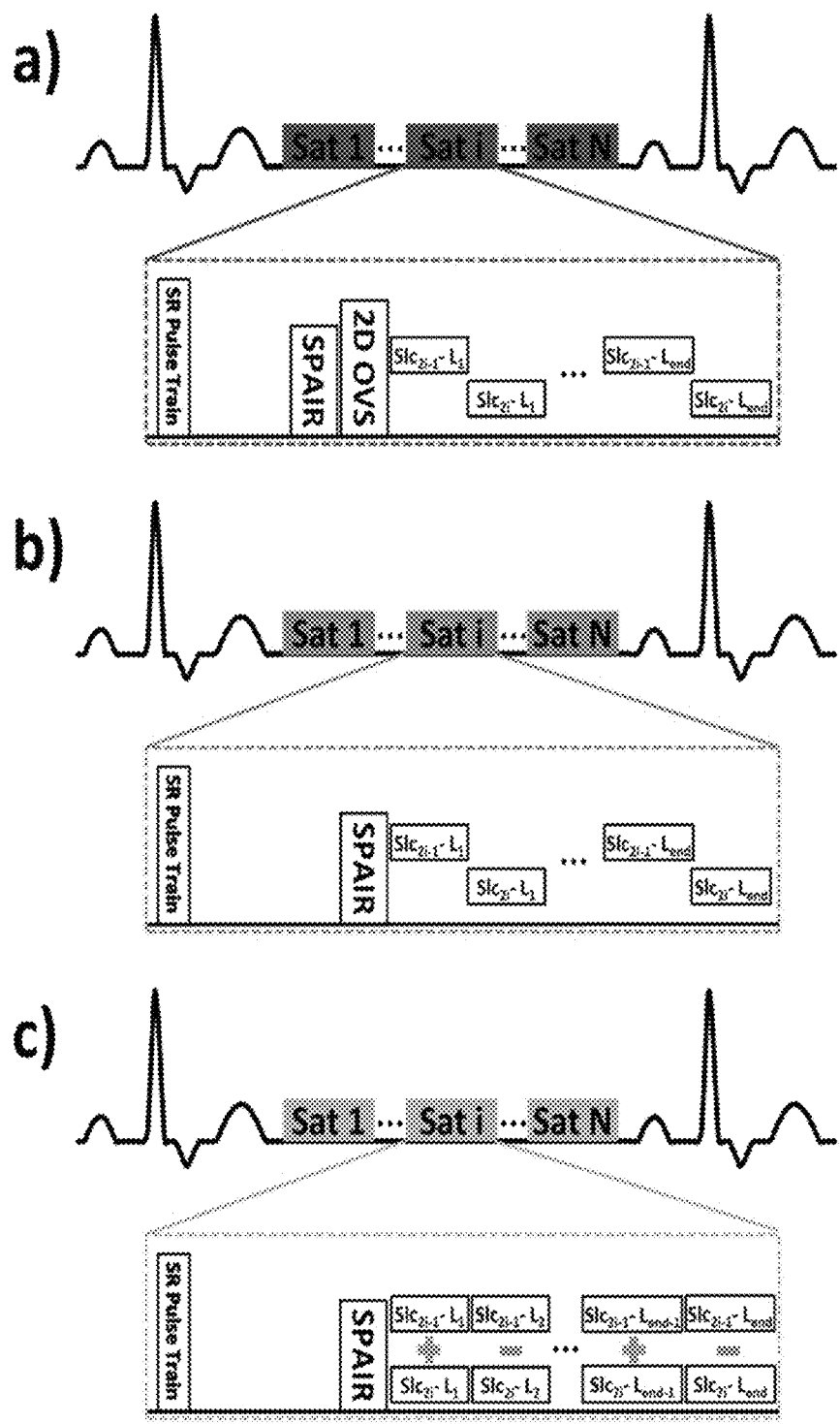
FIG. 14 shows pulse sequence schematics of (a) interleaved acquisition with outer-volume suppression (OVS), (b) interleaved acquisition without OVS and (c) SMS without OVS techniques.

Three different pulse sequences were evaluated, including an interleaved acquisition of two slices per saturation recovery (SR) block with OVS (FIG. 14 at (a)) and without OVS (FIG. 14 at (b)), and SMS with a multi band factor of 2 per SR without OVS (FIG. 14 at (c)). To further reduce the SAR, an optimized 5 hard-pulse SR was utilized ([8]). Resting first-pass perfusion using proposed sequences were performed with a 0.075 mmol/kg Dotarem bolus, separated by 20 min contrast washout time, in 5 healthy subjects on a 3T Prisma Siemens scanner. One subject was imaged using interleaved acquisition with and without OVS, while all other subjects were imaged by interleaved acquisition without OVS and SMS without OVS. The images were reconstructed by L1-SPIRiT or SMS-L1-SPIRiT using finite temporal difference as the sparsity transform. The image reconstruction was formulated as the following optimization problem:

$$\mathrm{argmin}_{x} \|\Phi DFx - y\|^2 + \lambda_1 \|(G-I)x\|^2 + \lambda_2 \|\Psi x\|_1,$$

where F Fourier transforms the data from the image domain to the k-space domain, D is the inverse gridding operator that transfers the Cartesian grid to the spiral trajectory, G is an image-space SPIRiT operator that represents the k-space self-consistency convolutions in the image domain, $\Psi$ is the finite time difference transform that operates on each individual coil separately to achieve sparsity in the temporal domain of image time series, $\Phi$ is the operator to combine multiple phase modulation slices to single SMS slice for SMS acquisition or $\Phi$=I for interleaved acquisition, $\lambda_1$ and $\lambda_2$ are parameters that balance the data acquisition consistency with calibration consistency and sparsity. An upfront scan without SMS was used to derive the calibration kernel. The overall image quality was graded by a single cardiologist based on 5 point scale (5-excellent, 1-poor).

Results

Figure 15:
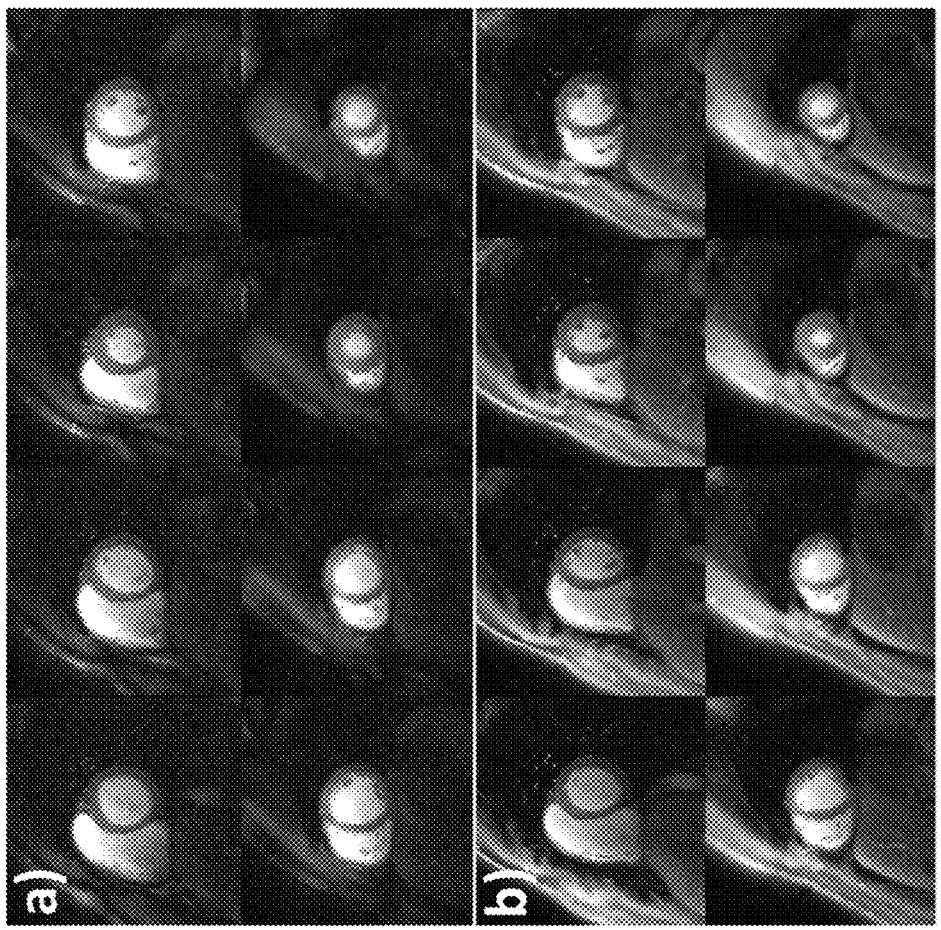
FIG. 15 shows a direct comparison of whole heart perfusion imaging at middle time frame using interleaved acquisition with OVS (a) and without OVS (b) from the same healthy subject.
Figure 16:
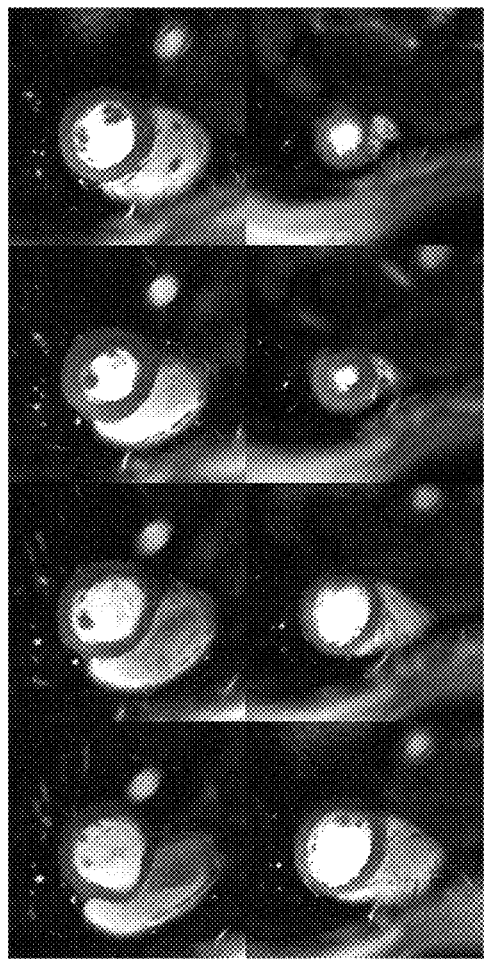
FIG. 16 shows an example case of 8 slices of 1.25 mm resolution perfusion images at middle time frame using interleaved acquisition pulse sequence without OVS.
Figure 17:
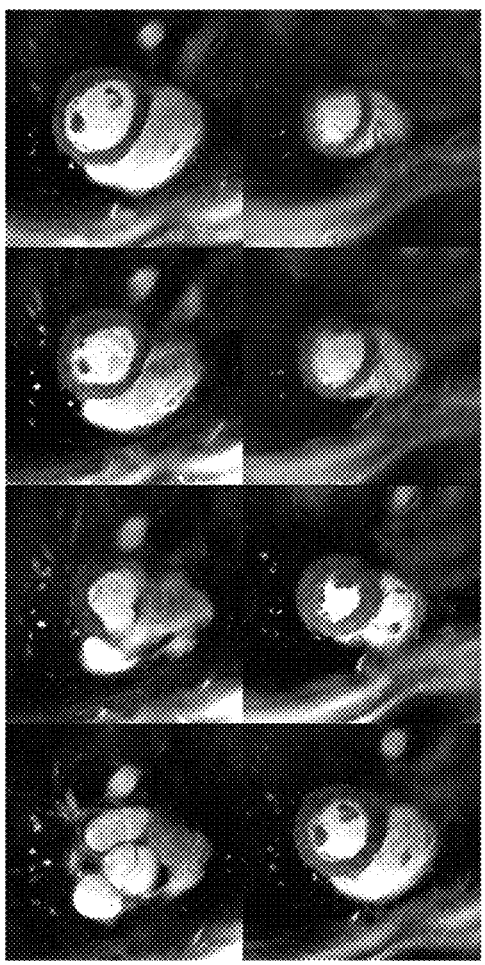
FIG. 17 shows an example case of 8 slices of 1.25 mm resolution perfusion images at middle time frame using SMS of MB=2 pulse sequence without OVS.

FIG. 15 shows the direct comparison of whole heart perfusion imaging at a middle time frame during first pass using interleaved acquisition with OVS (a) and without OVS (b) from the same healthy subject. The OVS can achieve good signal suppression outside the heart but requires higher SAR to achieve the necessary B1 field. Good image quality is achieved at 1.25 mm spatial resolution with or without OVS. Reduction of the acquisition time per interleaf from 5 ms to 4 ms improved image quality and reduced drop-out artifacts. FIG. 16 presents another example case with the same resolution at a similar time frame during first-pass of contrast using an interleaved acquisition pulse sequence without OVS. FIG. 17 shows perfusion images from the same subject acquired using the SMS MB=2 pulse sequence without OVS. Image quality scores were 4.6±0.2 and 4.0±0.7 for the interleaved and SMS techniques without OVS respectively. Either an interleaved acquisition or SMS strategy can produce high quality perfusion images with whole heart coverage and ultra-high spatial resolution without requiring the OVS module, which may improve applicability for stress perfusion imaging.

Conclusion

This example implementation shows the successful application of ultra-high resolution spiral perfusion sequence using interleaved acquisition and SMS techniques either with or without OVS. High resolution, whole heart perfusion may be used to quantify regional of the subendo and subepi myocardium. Further validation may be done in patients undergoing adenosine stress CMR.

Example 4

Figure 18:
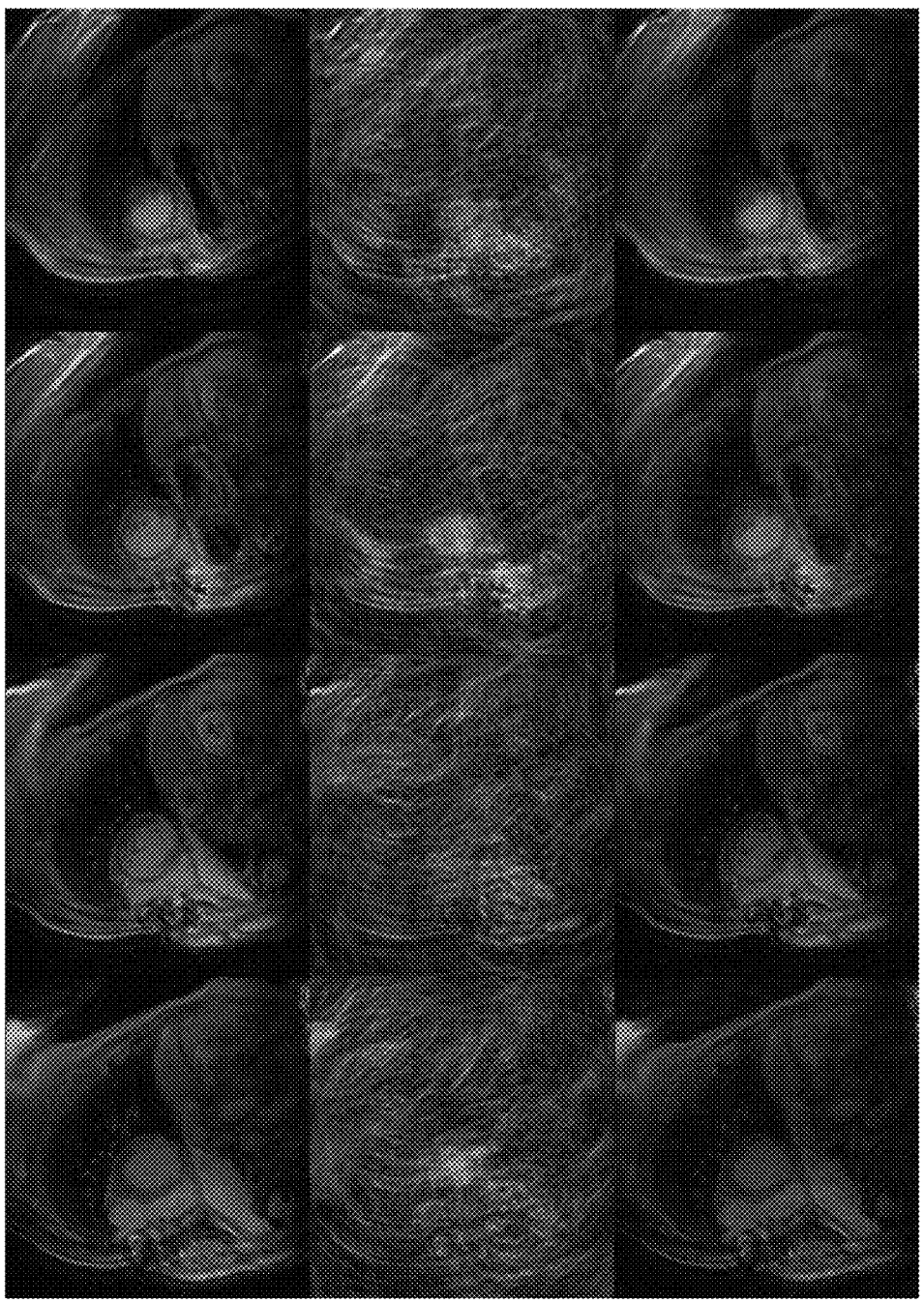
FIG. 18 shows an example of SMS spiral LGE image reconstruction in accordance with certain embodiments of the present disclosure. The first row shows the images acquired from 4 slice locations (from pig subject). The second row of data shows simulated data for one heartbeat of a 12 heartbeat acquisition acquired with spiral SMS with golden-angle rotation of spiral interleaves and Hadamard phase cycling with multi-band factor of 4 after phase demodulation for each of the slices. The third row shows a spiral SMS reconstruction, which recovers the ground truth images with minimal residual artifacts.

The following describes another example implementation of aspects of the present disclosure in accordance with some embodiments. FIG. 18 shows an example of SMS spiral LGE image reconstruction in accordance with certain embodiments of the present disclosure. The first row shows the images acquired from 4 slice locations (pig subject). The second row of data shows simulated data for one heartbeat of a 12 heart beat acquisition acquired with Spiral-SMS with golden-angle rotation of spiral interleaves and Hadamard phase cycling with multi-band factor of 4 after phase demodulation for each of the slices. Note the incoherent aliasing artifacts. The third row shows a spiral SMS reconstruction, which recovers the ground truth images with minimal residual artifacts. In this case, the reconstruction was performed by temporal summing of the data over the 12 heart beats following phase demodulation. This data can also be recovered using a more sophisticated reconstruction technique for more highly under sampled data.

Example 5

Figure 19:
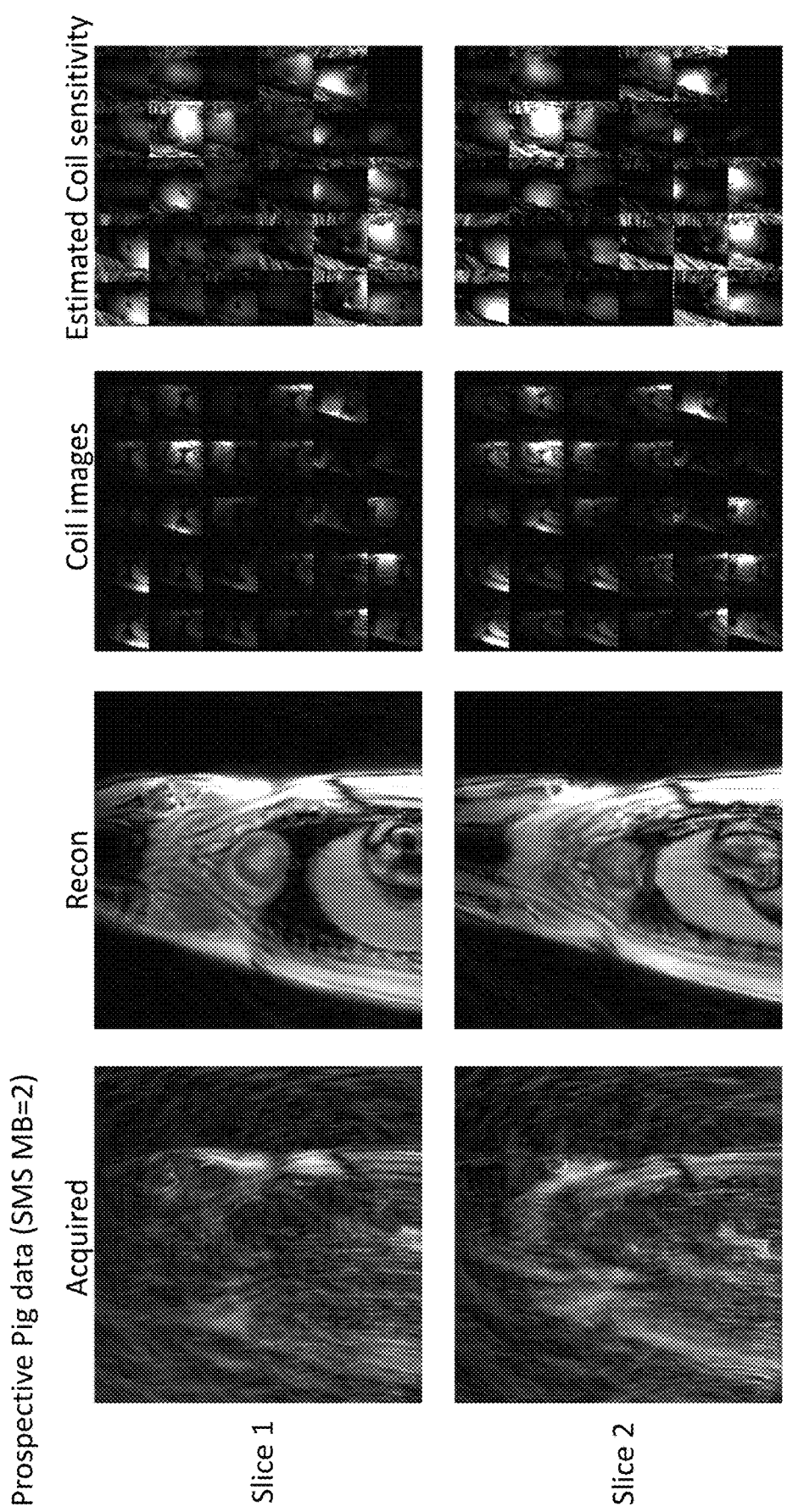
FIG. 19 shows an example of auto-calibration of coil sensitivity data from acquired image data, with prospective late gadolinium enhancement (LGE) pig data acquired using golden-angle spiral SMS with Hadamard phase cycling according to some embodiments of the present disclosure.

The following describes another example implementation of aspects of the present disclosure in accordance with some embodiments. FIG. 19 shows an example of auto-calibration of coil sensitivity data from acquired image data, with prospective late gadolinium enhancement (LGE) pig data acquired using golden-angle spiral SMS with Hadamard phase cycling according to some embodiments of the present disclosure. By temporally summing the data, each of the two slice images can be recovered without residual artifacts. This data can then be used to derive coil images and perform auto-calibrated estimates of the coil sensitivity data from each individual slice location which can be used for SENSE parallel imaging reconstruction, or for calibration of a GRAPPA or SPIRiT ([3]) kernel without an externally acquired calibration scheme.

Example 6

Figure 20:
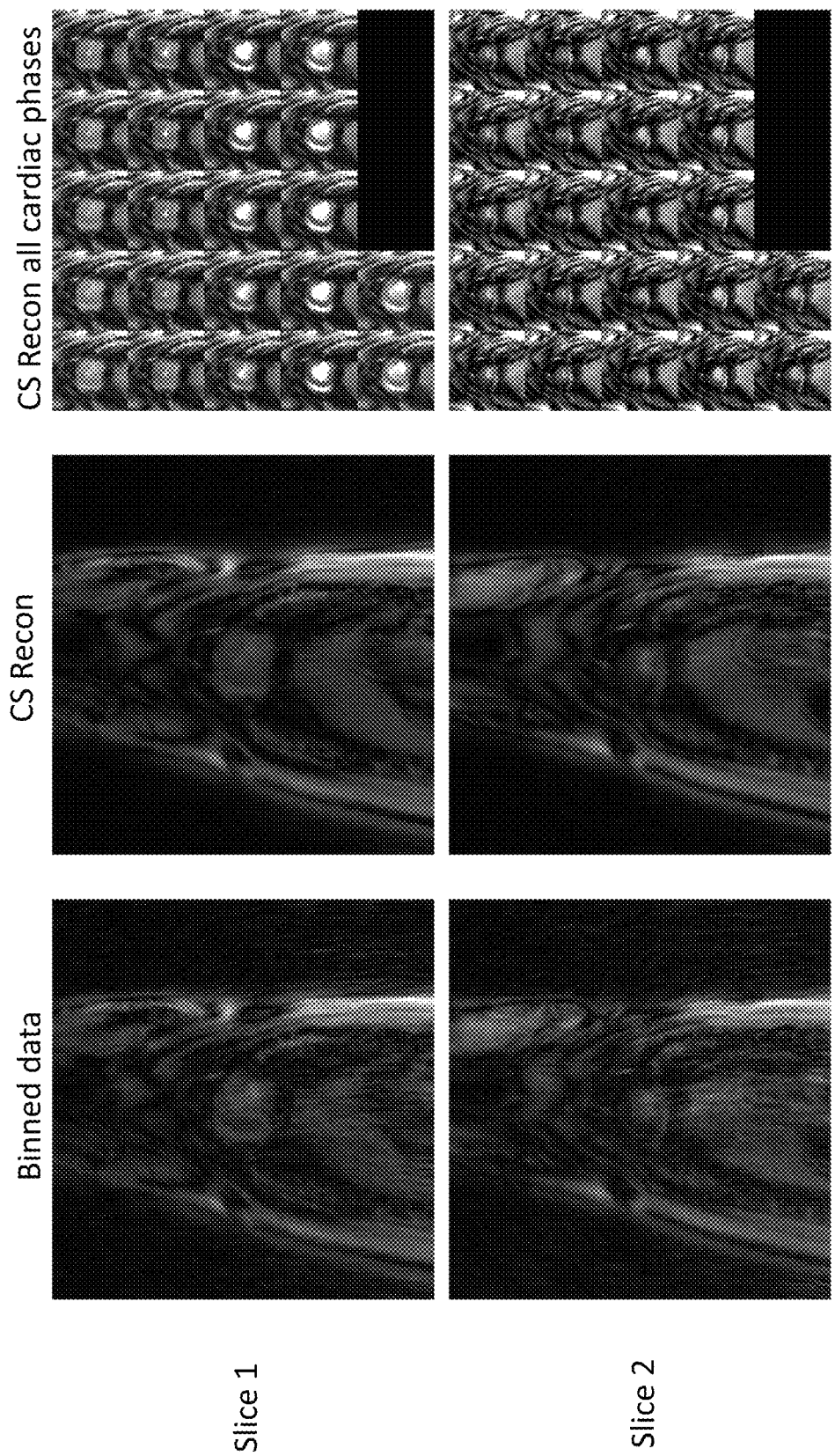
FIG. 20 shows an example of cine imaging (pig subject) wherein data is acquired simultaneously from two slice locations using Hadamard phase cycling and golden angle in time rotation of the spiral interleave. Data is binned into various cardiac phases based on the ECG or a self-gating signal.

The following describes another example implementation of aspects of the present disclosure in accordance with some embodiments. FIG. 20 shows an example of cine imaging (pig subject) wherein data is acquired simultaneously from two slice locations using Hadamard phase cycling and golden angle in time rotation of the spiral interleave. Data is binned into various cardiac phases based on the ECG or a self-gating signal. FIG. 20 shows the raw images for each slice location after binning and demodulation. Note that just from this process the images at each slice position are recovered. Using a compressed-sensing reconstruction L1-SPIRiT, high quality cine images can be produced. The last column shows cine frames at multiple phases throughout the cardiac cycle for the two slice positions.

CONCLUSION

The various embodiments described above are provided by way of illustration only and should not be construed to limit the scope of the disclosed technology. Those skilled in the art will readily recognize that various modifications and changes may be made to the disclosed technology and are intended to be embraced within the scope of the disclosed technology. The patentable scope of certain embodiments of the disclosed technology is indicated by the appended claims, rather than the foregoing description, and all changes that come within the meaning and range of equivalents thereof are intended to be embraced therein.

REFERENCE LIST

1. Breuer F A, Blaimer M, Heidemann R M, Mueller M F, Griswold M A, Jakob P M. 2005. Controlled aliasing in parallel imaging results in higher acceleration (caipirinha) for multi-slice imaging. Magn Reson Med. 53(3):684-691.
2. Souza S P, Szumowski J, Dumoulin C L, Plewes D P, Glover G. 1988. Sima: Simultaneous multislice acquisition of mr images by hadamard-encoded excitation. J Comput Assist Tomogr. 12(6):1026-1030.
3. Lustig M, Pauly J M. 2010. SPIRiT: Iterative self-consistent parallel imaging reconstruction from arbitrary k-space. Magn Reson Med. 64(2):457-471.
4. Zhou R, Huang W, Yang Y, Chen X, Weller D S, Kramer C M, Kozerke S, Salerno M. 2018. Simple motion correction strategy reduces respiratory-induced motion artifacts for k-t accelerated and compressed-sensing cardiovascular magnetic resonance perfusion imaging. Journal of cardiovascular magnetic resonance: official journal of the Society for Cardiovascular Magnetic Resonance. 20(1):6.
5. Meyer C H, Pauly J M, Macovski A, Nishimura D G. 1990. Simultaneous spatial and spectral selective excitation. Magnet Reson Med. 15(2):287-304.
6. Yang Y, Zhao L, Chen X, Shaw P W, Gonzalez J A, Epstein F H, Meyer C H, Kramer C M, Salerno M. 2017. Reduced field of view single-shot spiral perfusion imaging. Magnet Reson Med.
7. Salerno M, Taylor A, Yang Y, Kuruvilla S, Ragosta M, Meyer C H, Kramer C M. 2014. Adenosine stress cardiovascular magnetic resonance with variable-density spiral pulse sequences accurately detects coronary artery disease: Initial clinical evaluation. Circ Cardiovasc Imaging. 7(4):639-646.
8. Chow K, Kellman P, Spottiswoode B S, Nielles-Vallespin S, Arai A E, Salerno M, Thompson R B. 2015. Saturation pulse design for quantitative myocardial t1 mapping. Journal of Cardiovascular Magnetic Resonance 17:84.

What is claimed is:

1. A method for magnetic resonance imaging of a region of interest of a subject, comprising:
   simultaneously exciting multiple, different slice locations corresponding to a region of interest of a subject using a radio-frequency (rf) pulse, for obtaining multiple slices, wherein the excitation phase is modulated between acquisitions using a phase cycling scheme configured to create signal cancellation of all but one slice of the multiple excited slices from the different slice locations;
   applying an imaging pulse sequence using a spiral k-space trajectory to acquire image data from the multiple slices, for an image or series of images of the region of interest; and
   reconstructing, from the multiple slices, images of the region of interest, wherein the reconstructing recovers unaliased images from the different slice locations.

2. The method of claim 1, wherein the phase cycling scheme comprises a Hadamard excitation phase modulation pattern.

3. The method of claim 1, wherein the phase cycling scheme comprises a CAIPIRINHA (controlled aliasing in parallel imaging results in higher acceleration) technique.

4. The method of claim 1, wherein the phase of the excitation is rotated between excitations by the golden angle or a temporally uncorrelated matrix to create temporal incoherence of the residual aliasing pattern of the other slices to facilitate compressed sensing reconstruction.

5. The method of claim 1, wherein the reconstructing recovers unaliased images using coil sensitivity information from the multiple slice locations.

6. The method of claim 5, wherein the coil sensitivity information is derived from a calibration scan.

7. The method of claim 5, wherein the coil sensitivity information is derived via auto-calibration wherein a combination of the acquired image data, including the temporal average or other sub selection of data, is used to derive the coil sensitivity information.

8. The method of claim 1, wherein reconstructing the images of the region of interest comprises using a simultaneous-multi-slice (SMS) excitation extension of an L1-SPIRiT (iterative self-consistent parallel imaging reconstruction) reconstruction technique.

9. The method of claim 8, wherein the SMS excitation extension of the L1-SPIRiT reconstruction technique includes calibration for at least one of in-plane and through-slice parallel imaging.

10. The method of claim 1, wherein reconstructing the images of the region of interest comprises using a sensitivity encoding (SENSE) based multi-slice excitation reconstruction technique.

11. The method of claim 10, wherein the SENSE-based multi-slice excitation reconstruction technique includes calibration for at least one of in-plane and through-slice parallel imaging.

12. The method of claim 1, wherein the multiple slices are first separated using a pre-processing step prior to reconstruction of the data from each slice.

13. The method of claim 12, wherein the pre-processing step comprises Slice GRAPPA (generalized autocalibrating partially parallel acquisitions).

14. The method of claim 1, wherein the pulse sequence is configured to collect a temporal series for cine imaging of heart function.

15. The method of claim 1, wherein the pulse sequence is applied during or following introduction of a contrast agent to the subject.

16. The method of claim 1, further comprising creating one or more parametric maps of magnetic relaxation parameters including at least one of T1, T2, T2*, T1ρ, magnetization transfer (MT), chemical exchange (CEST), and diffusion.

17. The method of claim 1, wherein the region of interest comprises the heart of the subject.

18. A method for perfusion magnetic resonance imaging of a subject, comprising:
    simultaneously exciting multiple, different slice locations corresponding to a region of interest of a subject using a radio-frequency (rf) pulse, for obtaining multiple slices, wherein the excitation phase is modulated between acquisitions using a phase cycling scheme configured to create signal cancellation of all but one slice of the multiple excited slices from the different slice locations;
    applying an imaging pulse sequence using a spiral k-space trajectory to acquire imaging data from the multiple slices, for an image or series of images of the region of interest;
    rotating the phase of the excitation between heartbeats of the subject to create temporal incoherence of a residual aliasing pattern of aliasing; and
    reconstructing, from the multiple slices, images of the region of interest.

19. The method of claim 18, wherein the reconstructing recovers unaliased images using coil sensitivity information from the different slice locations and a compressed sensing-based reconstruction technique.

20. The method of claim 18, wherein the phase of the excitation is rotated between excitations by the golden angle or a temporally uncorrelated matrix to create temporal incoherence of the residual aliasing pattern of the other slices to facilitate compressed sensing reconstruction.

21. The method of claim 18, wherein the phase cycling scheme comprises a Hadamard excitation phase modulation pattern.

22. The method of claim 18, wherein the phase cycling scheme comprises a CAIPIRINHA (controlled aliasing in parallel imaging results in higher acceleration) technique.

23. The method of claim 19, wherein the coil sensitivity information is derived from a calibration scan.

24. The method of claim 19, wherein the coil sensitivity information is derived via auto-calibration wherein a combination of the acquired image data, including the temporal average or other sub selection of data, is used to derive the coil sensitivity information.

25. The method of claim 18, wherein reconstructing the images of the region of interest comprises using a simultaneous-multi-slice (SMS) excitation extension of an L1-SPIRiT (iterative self-consistent parallel imaging reconstruction) reconstruction technique.

26. The method of claim 25, wherein the SMS excitation extension of the L1-SPIRiT reconstruction technique includes calibration for at least one of in-plane and through-slice parallel imaging.

27. The method of claim 18, wherein reconstructing the images of the region of interest comprises using a sensitivity encoding (SENSE) based multi-slice excitation reconstruction technique.

28. The method of claim 27, wherein the SENSE-based multi-slice excitation reconstruction technique includes calibration for at least one of in-plane and through-slice parallel imaging.

29. The method of claim 18, wherein the multiple slices are first separated using a pre-processing step prior to reconstruction of the data from each slice.

30. The method of claim 29, wherein the pre-processing step comprises Slice GRAPPA (generalized autocalibrating partially parallel acquisitions).

31. The method of claim 18, wherein the pulse sequence is applied during or following introduction of a contrast agent to the subject.

32. The method of claim 18, further comprising creating one or more parametric maps of magnetic relaxation parameters including at least one of T1, T2, T2*, T1ρ, magnetization transfer (MT), chemical exchange (CEST), and diffusion.

33. A method for magnetic resonance imaging of a region of interest of a subject, comprising:
    simultaneously exciting multiple, different slice locations corresponding to a region of interest of a subject using a radio-frequency (rf) pulse, for obtaining multiple slices, wherein the excitation phase is modulated between acquisitions using a phase cycling scheme configured to create signal cancellation of all but one slice of the multiple excited slices from the different slice locations;
    applying an imaging pulse sequence using a non-Cartesian trajectory to acquire imaging data from the multiple slices, for an image or series of images of the region of interest; and
    reconstructing, from the multiple slices, images of the region of interest, wherein the reconstructing recovers unaliased images from the different slice locations, and wherein the phase of the excitation is rotated between excitations by the golden angle or a temporally uncorrelated matrix to create temporal incoherence of the residual aliasing pattern of the other slices to facilitate compressed sensing reconstruction.

34. A method for magnetic resonance imaging of a region of interest of a subject, comprising:
    simultaneously exciting multiple, different slice locations corresponding to a region of interest of a subject using a radio-frequency (rf) pulse, for obtaining multiple slices, wherein the excitation phase is modulated between acquisitions using a phase cycling scheme configured to create signal cancellation of all but one slice of the multiple excited slices from the different slice locations;

applying a variable density Cartesian pulse sequence to acquire image data from the multiple slices, for an image or series of images of the region of interest; and reconstructing, from the multiple slices, images of the region of interest, wherein the reconstructing recovers unaliased images from the different slice locations.

35. A system for magnetic resonance imaging of a region of interest of a subject, comprising:

an excitation pulse generator configured to generate a radio-frequency (rf) pulse to simultaneously excite multiple, different slice locations corresponding to a region of interest of a subject, for obtaining multiple slices, wherein the excitation phase is modulated between acquisitions using a phase cycling scheme configured to create signal cancellation of all but one slice of the multiple excited slices from the different slice locations;

an imaging data acquisition system configured to acquire image data from the multiple slices, for an image or series of images of the region of interest by applying an imaging pulse sequence using a spiral k-space trajectory or a variable density Cartesian pulse sequence; and a processor coupled to the excitation pulse generator and imaging data acquisition system and configured to cause the system to perform functions to reconstruct, from the multiple slices, images of the region of interest, wherein the reconstructing recovers unaliased images from the different slice locations.

* * * * *